(12) United States Patent
Brands et al.

(10) Patent No.: US 8,735,087 B2
(45) Date of Patent: May 27, 2014

(54) USE OF ALKALINE PHOSPHATASE FOR PREVENTING OR REDUCING LIVER DISEASE

(71) Applicant: PharmAAware Sepsis B.V., Bunnik (NL)

(72) Inventors: Rudi Brands, Bunnik (NL); Klaas Poelstra, Buitenpost (NL)

(73) Assignee: PharmAAware Sepsis B.V., Bunnik (NL)

( * ) Notice: Subject to any disclaimer, the term of this patent is extended or adjusted under 35 U.S.C. 154(b) by 0 days.

(21) Appl. No.: 13/768,866

(22) Filed: Feb. 15, 2013

(65) Prior Publication Data

US 2013/0280232 A1 Oct. 24, 2013

Related U.S. Application Data

(63) Continuation of application No. 10/588,285, filed as application No. PCT/NL2005/000084 on Feb. 4, 2005, now Pat. No. 8,574,863.

(60) Provisional application No. 60/541,363, filed on Feb. 4, 2004.

(30) Foreign Application Priority Data

Feb. 4, 2004 (EP) ..................................... 04075344

(51) Int. Cl.
*C12Q 1/42* (2006.01)

(52) U.S. Cl.
USPC ............................................................ 435/21

(58) Field of Classification Search
USPC ......................................................... 435/21
See application file for complete search history.

(56) References Cited

U.S. PATENT DOCUMENTS

| | | | |
|---|---|---|---|
| 5,567,724 A | 10/1996 | Kelleher et al. | |
| 6,290,952 B1 * | 9/2001 | Poelstra et al. | ............... 424/94.2 |
| 6,406,899 B1 | 6/2002 | Hoelke et al. | |
| 7,157,260 B2 | 1/2007 | Mori et al. | |
| 7,856,139 B2 | 12/2010 | Chen | |
| 2009/0010912 A1 | 1/2009 | Brands et al. | |
| 2010/0016313 A1 | 1/2010 | Millan | |
| 2010/0111923 A1 | 5/2010 | Pickkers et al. | |
| 2010/0143323 A1 | 6/2010 | Velders et al. | |
| 2010/0158888 A1 | 6/2010 | Kiss | |
| 2011/0052560 A1 | 3/2011 | Brands | |
| 2011/0142817 A1 | 6/2011 | Brands et al. | |
| 2011/0206654 A1 | 8/2011 | Hodin et al. | |

FOREIGN PATENT DOCUMENTS

| | | |
|---|---|---|
| EP | 1 733 734 A2 | 12/2006 |
| JP | 09-172962 A | 7/1997 |
| JP | 2003/146888 | 5/2003 |
| WO | WO 93/18139 A1 | 9/1993 |
| WO | WO 95/05456 A1 | 2/1995 |
| WO | WO 96/39203 A1 | 12/1996 |
| WO | WO 00/37943 | 6/2000 |
| WO | WO 02/06214 A1 | 1/2002 |
| WO | WO 02/056900 A2 | 7/2002 |
| WO | WO 02/057430 A2 | 7/2002 |
| WO | WO 02/098433 A1 | 12/2002 |
| WO | WO 03/015817 A2 | 2/2003 |
| WO | WO 2010/025267 A2 | 3/2010 |
| WO | WO 2012/169892 A2 | 12/2012 |

OTHER PUBLICATIONS

Beumer, C., et al., "Calf Intestinal Alkaline Phosphatase, a Novel Therapeutic Drug of Lipopolysaccharide (LPS)-Mediated Diseases, Attenuates LPS Toxicity in Mice and Piglets," *The Journal of Pharmacology and Experimental Therapeutics* 307(2):737-744(2003).
English language Abstract and machine translation of Japanese Patent Publication No. 09-172962 A, Japanese Patent Office, Jul. 8, 1997.
Eriksson HJ, et al., "Investigations into the stabilization of drugs by sugar glasses: Delivery of an inulin-stabilised alkaline phosphatase in the intestinal lumen via the oral route" *Int J Pharm.* 257:273-81 (2003).
Harms, G. et al., "Immunopathology of Alkaline Phosphatase-induced Granulomatous Hepatitis in Rats," *Virchows Archiv B Cell Pathol* 62:35-43(1992).
Koyama, I., et al., "Alkaline Phosphatases Reduce Toxicity of Lipopolysaccharides In Vivo and In Vitro Through Dephosphorylation," *Clinical Biochemistry* 35:455-461(2002).
Nugent, SG, et al., "Intestinal luminal pH in inflammatory bowel disease: possible determinants and implications for therapy with aminosalicytates and other drugs" *Gut* 48:571-577 (2001).
Poelestra, K., et al., Dephosphorylation of Endotoxin by Alkaline Phosphatase In Vivo.et al., *American Journal of Pathology* 151 (4):1163-1169(1997).
Shahani, K.M., et al., "Enzymes in bovine milk: a review," *Journal of Dairy Science* 56(5):531-543(1973).

* cited by examiner

*Primary Examiner* — Ralph Gitomer
(74) *Attorney, Agent, or Firm* — Sterne, Kessler, Goldstein & Fox P.L.L.C.

(57) ABSTRACT

The present invention provides a use for alkaline phosphatase for the manufacture of a medicament for the prevention or reduction of toxic LPS influx through a mucosal lining of a mammalian body cavity. A source of alkaline phosphatase is administered for the prophylaxis or treatment of LPS mediated or exacerbated diseases. The invention also provides compositions comprising a source of alkaline phosphatase for the prevention or reduction of (toxic) LPS influx or passage through mucosal layers.

8 Claims, 10 Drawing Sheets

Figure 1:
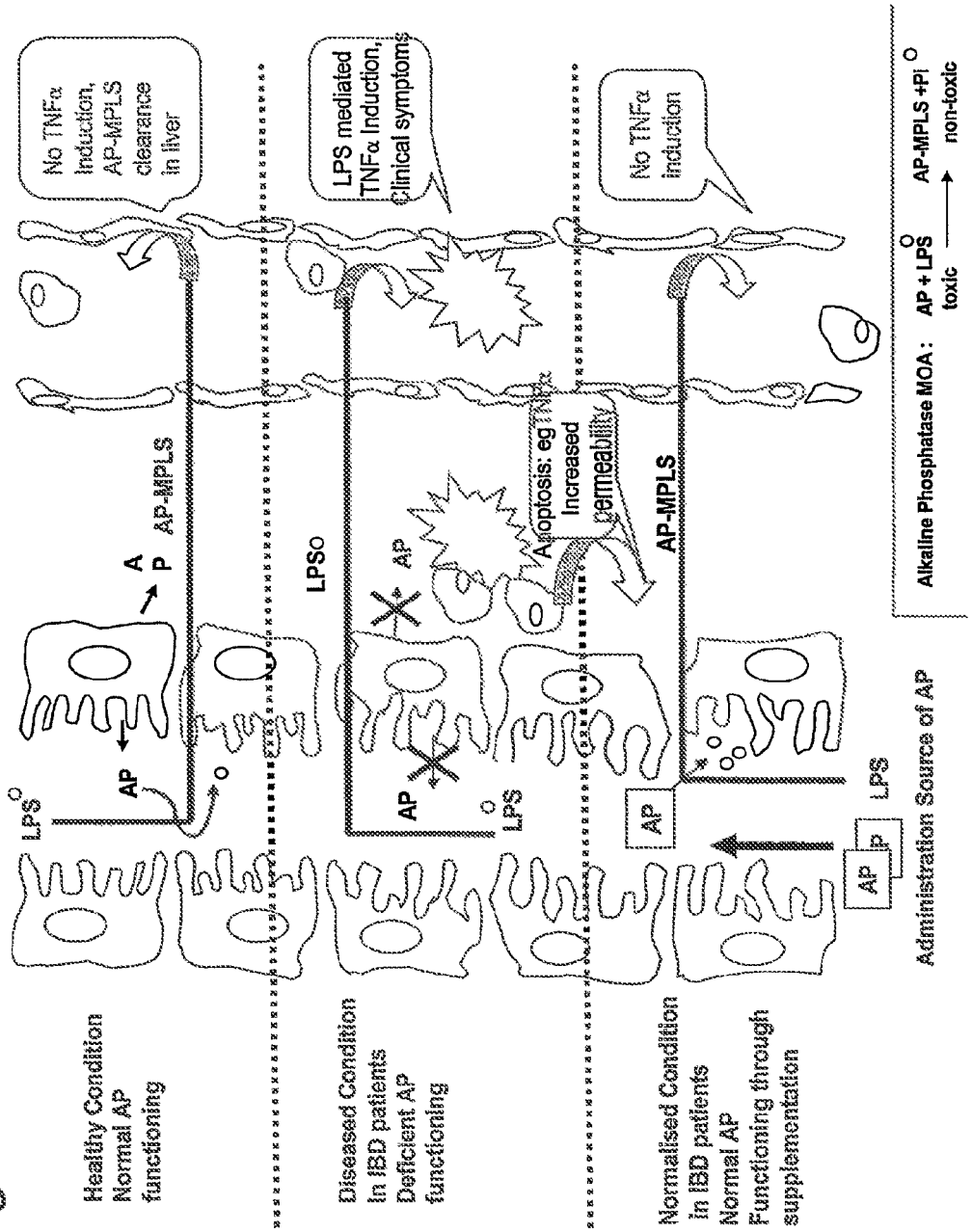

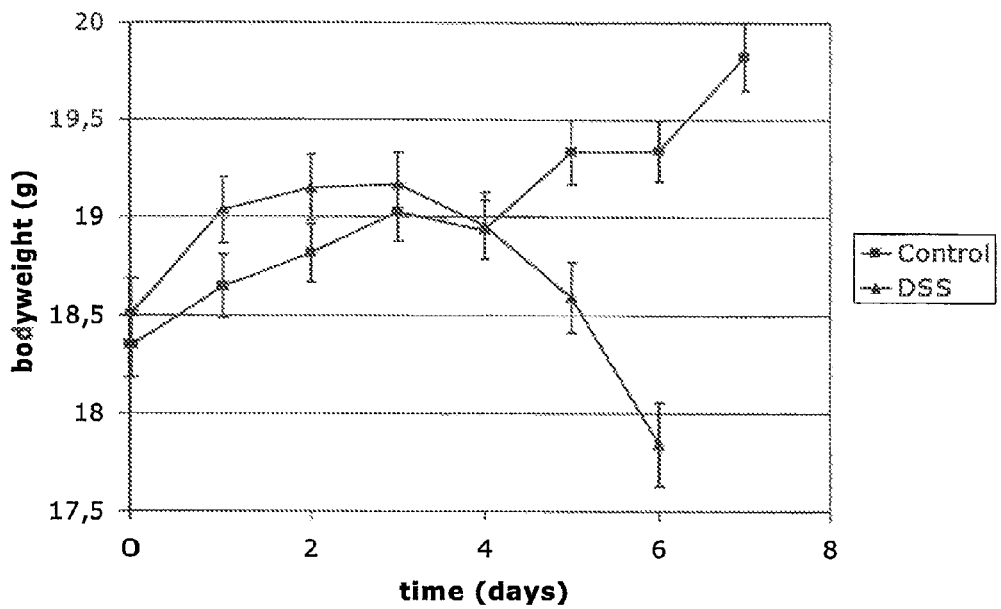
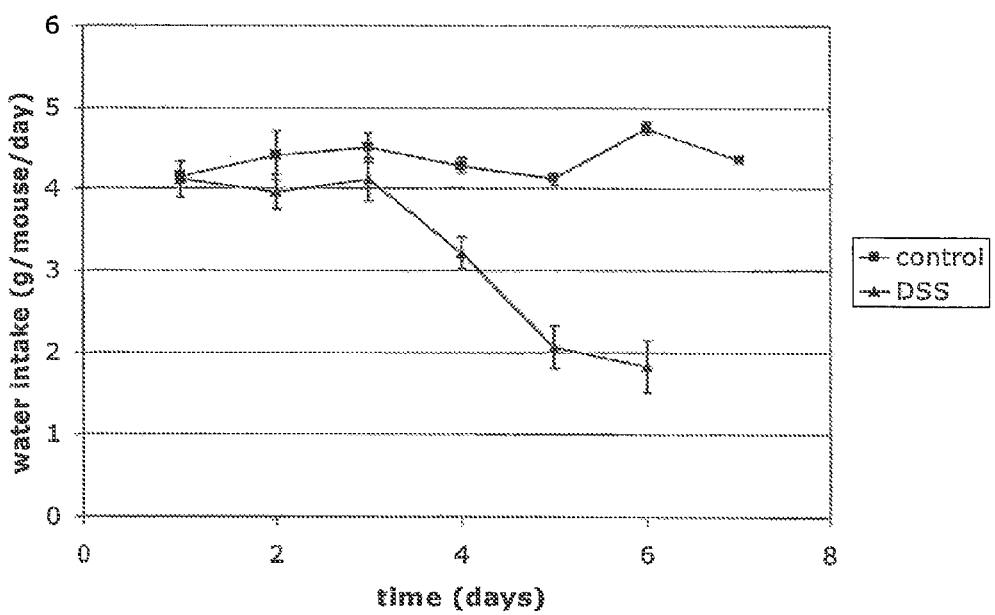

USE OF ALKALINE PHOSPHATASE FOR PREVENTING OR REDUCING LIVER DISEASE

CROSS REFERENCE TO RELATED APPLICATIONS

This application is a continuation of U.S. application Ser. No. 10/588,285 now issued U.S. Pat. No. 8,574,863, which is a U.S. National Stage application of Int Appl. No. PCT/NL2005/000084, filed Feb. 4, 2005, which claims priority from U.S. Provisional Application No. 60/541,363, filed Feb. 4, 2004 and EP Appl. No. 04075344.4, filed Feb. 4, 2004, each of which is incorporated herein by reference in its entirety.

FIELD OF THE INVENTION

The current invention relates to the field of medicine and in particular to the use of LPS detoxifying and neutralizing enzymes. The present invention also relates to the field of pharmacy and in particular to the pharmaceutical use of alkaline phosphatase enzymes.

BACKGROUND OF THE INVENTION

Lipopolysaccharides (LPS; also referred to as endotoxins) are present in the cell walls of Gram-negative bacteria. When LPS is presented to a vertebrate body it stimulates the innate and cellular immune responses in a wide variety of cell types. The production of cytokines and chemokines (such as TNF's, various interleukines, interferons and others) will attract and activate cells of the immune system, which may culminate ultimately in an LPS induced systemic inflammatory response syndrome (SIRS) under certain conditions.

LPS or endotoxins are toxic to most mammals and regardless of the bacterial source, all endotoxins produce the same range of biological effects in the animal host. The injection of living or killed Gram-negative cells, or purified LPS, into experimental animals causes a wide spectrum of non-specific pathophysiological reactions such as: fever, tachycardia, tachypneu, hyper or hypothermia, changes in white blood cell counts, disseminated intravascular coagulation, hypotension, organ dysfunction and may even result in shock and death.

Injection of small doses of endotoxin results in a proinflammatory response in most mammals, but the dose response range and steepness thereof varies significantly with the species and even within species may differ significantly depending on e.g. LPS-tolerance. The sequence of pro-inflammatory events follows a regular pattern (inflammatory cascade): (1) latent period; (2) physiological distress (diarrhea, prostration, shock); and in case of severe septic shock and multiple organ failure may result in (3) death. How soon death occurs varies on the dose of the endotoxin, route of administration, and species of animal.

The physiological effects of endotoxin are mainly mediated by the lipid A-moiety of LPS. Since Lipid A is embedded in the outer membrane of bacterial cells, it only exerts its toxic effects when released from multiplying cells in a soluble form, or when the bacteria are lysed as a result of autolysis, complement and the membrane attack complex (MAC), ingestion and killing by phagocytes, or killing with certain types of antibiotics. LPS released into the bloodstream can be neutralised by many blood components to a certain degree, amongst which several plasma lipids and proteins, among which LPS-binding proteins. The LPS-binding protein complex interacts with CD 14 and Toll like receptors on monocytes and macrophages and through other receptors on endothelial cells. In monocytes and macrophages three types of events are triggered during their interaction with LPS:

Firstly, production of cytokines, including IL-1, IL-6, IL-8, tumor necrosis factor (TNF) and platelet-activating factor. These in turn stimulate production of prostaglandins and leukotrienes. These are powerful mediators of inflammation and septic shock that accompanies endotoxin toxemia. LPS activates macrophages to enhanced phagocytosis and cytotoxicity. Macrophages are stimulated to produce and release lysosomal enzymes, IL-1 ("endogenous pyrogen"), and tumor necrosis factor (TNFalpha), as well as other cytokines and mediators.

Secondly, activation of the complement cascade. C3a and C5a cause histamine release (leading to vasodilation) and effect neutrophil chemotaxis and accumulation. The result is inflammation.

Finally, activation of the coagulation cascade. Initial activation of Hageman factor (blood-clotting Factor XII) can activate several humoral systems resulting in coagulation: a blood clotting cascade that leads to coagulation, thrombosis, acute disseminated intravascular coagulation, which depletes platelets and various clotting factors resulting in internal bleeding and also activation of the complement alternative pathway (as above, which leads to inflammation). Plasmin is activated which leads to fibrinolysis and hemorrhaging and kinin activation releases bradykinins and other vasoactive peptides which causes hypotension. The net effect is induction of inflammation, intravascular coagulation, hemorrhage and shock.

LPS also acts as a B cell mitogen stimulating the polyclonal differentiation and multiplication of B-cells and the secretion of immunoglobulins, especially IgG and IgM.

The physiological activities of LPS are mediated mainly by the Lipid A component of LPS. Lipid A is a powerful biological response modifier that can stimulate the mammalian immune system. During infectious disease caused by Gram-negative bacteria, endotoxins released from, or part of, multiplying cells have similar effects on animals and significantly contribute to the symptoms and pathology of the disease encountered. The primary structure of Lipid A has been elucidated and Lipid A has been chemically synthesized. Its biological activity appears to depend on a peculiar conformation that is determined by the glucosamine disaccharide, the $PO_4$ groups, the acyl chains, and also the KDO-containing inner core of the LPS molecule.

Alkaline phosphatase (AP), has been described earlier as a key enzyme in the dephosphorylation of LPS (endotoxin) under physiological conditions both in vitro and in vivo as a natural response to detoxify and neutralise LPS (U.S. Pat. No. 6,290,952, Poelstra et al, Am J Pathol. 1997 October; 151(4): 1163-9).

Reports on the enzyme activity of AP involve its extremely high pH optimum for the usual exogenous substrates and its localization as an ecto-enzyme. Endotoxins are molecules that contain several phosphate groups and are usually present in the extracellular space. AP is able to dephosphorylate this bacterial product at physiological pH levels, by removing phosphate groups from amongst others the toxic lipid A moiety of LPS. As phosphate residues in the lipid A moiety determine the toxicity of the molecule, the effect of the AP inhibitor levamisole in vivo using a septicemia model in the rat confirmed the specificity of AP for LPS containing phosphate groups (Poelstra et al., 1997). The results demonstrated that inhibition of endogenous AP by levamisole significantly reduces survival of rats intraperitoneally injected with *E. coli* bacteria, whereas this drug does not influence survival of rats receiving a sublethal dose of the gram-positive bacteria *Sta-*

*phylococcus aureus*, illustrating a crucial role for this enzyme in host defense. The effects of levamisole during gram-negative bacterial infections and the localization of AP as an ecto-enzyme in most organs as well as the induction of enzyme activity during inflammatory reactions and cholestasis is in accordance with such a protective role.

The prime source of LPS exposure in the human body are the gram negative microorganisms that live within the human digestive or gastrointestinal (GI) tract. There are far more bacteria in the digestive system than there are on the skin or other parts of the body, making the GI tract and GI mucosa the main route of entry for LPS into the circulation. An average adult carries about 100 trillion bacteria in the intestines, most of which locate in the colon, contributing to 1-1.5 kg of his body weight. There are more than 400 species of bacteria found in the digestive system. These include both beneficial (commensal) and potentially harmful (pathogenic) species, which continually compete to maintain a well-balanced intestinal flora.

Mucosal surfaces, and in particular (but not limited to) the intestinal mucosa, are exposed to this wide variety of commensal and potentially pathogenic bacteria, among which many gram negative endotoxin/LPS producing, Gram-negative bacteria such as *E. coli, Salmonella, Shigella, Pseudomonas, Neisseria, Haemophilus, Helicobacter, Chlamydia* and other leading pathogens. The intestinal epithelium is of particular importance as it forms a dynamic barrier that regulates absorption of nutrients and water and at the same time restricts uptake of microbes and other noxious materials such as LPS from the gut lumen.

It is well established that a major fraction of LPS influx from the lumen of the gut through the mucosal lining into the circulation of a vertebrate body is mediated through chylomicrons (Harris et al., 1998, 2000, 2002). Coincidental with ingestion of lipids and chylomicron introduction in circulation, capable of carrying LPS, a significant increase in lymphatic AP derived from the GI-tract is reported (Nauli et al., 2002). LPS-influx through the GI-barrier is increased normally with a saturated fat-rich diet. LPS inserts with its lipid A acyl chain into lipoprotein phospholipids. Thereby LPS passes the intestinal barrier by co-migrating with chylomicrons, that are taken up predominantly at the small intestines ileum (Harris et al., 2002). After a fat rich food intake a significant rise of glycosyl-phosphatidyl-inositol (GPI)-anchored AP complexed to lipoproteins is detected in lymph as well (Nauli et al., 2003).

The physiological roles of- and the interpretation of AP serum levels are not clear, but a role in detoxification of LPS has emerged from current research. The co-presence of both AP and LPS in chylomicron rich fractions suggest a role for AP in dephosphorylating the gut derived-LPS already at close vicinity. Detoxification can take place both in the intestinal lumen or en-route to or upon presentation to the liver, specifically in this context to Kuppfer cells and the hepatocytes, which clear the chylomicrons from circulation.

Increased serum AP levels are associated with hepatic damage. Upon an endotoxin insult, circulatory AP is redirected to hepatocytes, thereby reducing circulating AP levels initially (Bentala et al., 2002) through receptor-mediated uptake (asialo-glycoprotein receptor). Hepatocytes also remove the LPS-loaded chylomicrons (Harris et al., 2002) rapidly from circulation with a half life of 5-10 minutes. LPS is next removed through biliary excretion, thereby preventing Kuppfer cells, being a major target for circulating LPS to become activated (Harris, 2002). Bentala et al., 2002, showed that Kuppfer cells accumulate AP in LPS-insulted animal models as well. This may imply that under normal conditions Kuppfer cells will not be activated since LPS (lipidA moiety), or its derivative MPLS (MPLA, derivative from Lipid A), is primarily presented to hepatocytes through a lipoprotein receptor and next is removed via biliary secretion. However under conditions with excess LPS, Kupffer cells are activated through a TLR-4 (LPS) receptor.

A wide array of animals have AP and several other entities present to counteract a (bacterial) insult, either local or systemic, induced or available as guard/watchdog function. Amongst others activated neutrophils or macrophages express a wide array of inflammatory mediators destined to neutralise the insult. Moieties like, but not restricted to LPS binding protein (LBP), CD14, Apo-E, VLDL, HDL, albumin, immunoglobulin and AP all have been described to serve this function. When such an insult however is not overcome, e.g. in case of a severe Gram negative or positive insult, resulting inflammatory mediators may initiate a systemic inflammatory response syndrome (SIRS).

It was postulated that AP is consumed as a consequence of its catalytic action towards LPS (Poelstra et al., 1997). This implies that subsequently normal levels are to be restored through a controlled mechanism. In patients suffering from septicaemia, it has been observed that increased serum AP may be preceded by reduced AP serum levels (Manintveld and Poelstra, patent application EP 989626940) and that circulating AP would be cleared from circulation upon LPS interaction (Bentala et al., 2002). The increase in subsequent AP-levels therefore may be a feedback mechanism in response to this AP reduction. A mechanism for such a LPS/AP responsiveness has not been depicted to-date.

In inflammatory processes (temporary) increases are found for serum AP. In the context of this invention such an increase of AP is regarded as a natural response of the innate immune system to an LPS insult to tackle these insults and restore natural balance. Increased AP plasma levels are the result of massive shedding of AP from hepatocytes in response to the LPS insult. It has been observed that LPS induces Phospholipase-D activity (Locati et al., 2001) which in turn has been reported to act upon GPI anchored proteins, amongst which AP (Deng et al., 1996) and e.g. CD14, thereby effectively shedding the proteins into circulation (Zhang F et al., 2001, Locati M et al., 2001).

Circulating plasma AP—predominantly anchorless liver-type AP (Ahn et al., 2001)—may thus already have exerted its LPS detoxificating activity at the plasma membrane surface and is subsequently freed from the hepatocyte membrane into circulation prior to its subsequent elimination from circulation by e.g. the asialo glycoprotein-route.

AP exerts its catalytic activity towards LPS primarily in the vicinity of a membrane, possibly in so-called lipid rafts (drm or detergent-resistant membrane fraction) where it has been reported to reside. Several publications favor such a catalytic activity of AP at a membrane surface, either presented at the tissue level or released into circulation like with circulating liver plasma membrane fragments (LPMF) (e.g. Deng et al., 1996). The increased AP levels observed in chronically inflamed patients may be caused by the suboptimal detoxification of the gut-derived influx of LPS, which is often enhanced under pathological conditions prior to mobilization of hepatic AP.

The treatment of inflammatory diseases accounts for a substantial percentage of the gross medical cost in developed countries and the incidence of these inflammatory diseases is continuously rising due to key factors like ageing of the population and an increasing number of patients having suppressed immune systems as a consequence of medication and treatment of a wide array of diseases like heart disease, autoimmunity disorders and allergies, organ transplantations, cancer chemo- or radiotherapy and infectious diseases like AIDS. To a certain extent these diseases relate to an influx of bacterial LPS. The influx of LPS is often enhanced by a medical condition of a subject, causing an inflammatory process by a malfunctioning or non-balanced innate immune system, which constitutes the first line of defense against e.g. microbial insults, in particular from LPS/endotoxin producing bacteria.

The current invention is aimed at providing new methods and compositions for the detoxification, neutralisation or complexation of LPS in situ at mucosal tissues in body cavities before LPS can pass through the mucosal layer and enter the circulation where it would elicit toxic effects and/or an inflammatory response.

DESCRIPTION

Definitions

Endotoxins are part of the outer membrane of the cell wall of Gram-negative bacteria. Endotoxins are invariably associated with Gram-negative bacteria whether the organisms are pathogens or not. Although the term "endotoxin" is occasionally used to refer to any cell-associated bacterial toxin, it is properly reserved to refer to the lipopolysaccharide or LPS complex associated with the outer membrane of Gram-negative bacteria such as Escherichia (E. coli), Salmonella, Shigella, Pseudomonas (Ps. aeruginosa), Neisseria (N. meningitidis), Haemophilus (H. influenzae), Chlamydia (Chl. pneumoniae), Helicobacter (H. pylori) and other leading pathogens.

Lipopolysaccharides are complex amphiphilic molecules with a monomeric molecular weight of about 10 kDa, that vary widely in chemical composition both between and among bacterial species. LPS consists of three components or regions, Lipid A, an R polysaccharide and an O polysaccharide. Lipid A contains the hydrophobic, membrane-anchoring region of LPS. Lipid A consists of a phosphorylated N-acetyl-glucosamine (NAG) dimer with 6 or 7 fatty acids (FA) attached. The Core (R) antigen or R polysaccharide is attached to the 6 position of one NAG. The R antigen consists of a short chain of sugars. Two unusual sugars are usually present, heptose and 2-keto-3-deoxyoctonoic acid (KDO), in the core polysaccharide. KDO is unique and invariably present in LPS and so has been an indicator in assays for LPS (endotoxin).

With minor variations, the core polysaccharide and lipid A is common to all members of a bacterial genus (e.g. Salmonella), but it is structurally distinct in other genera of Gram-negative bacteria. Salmonella, Shigella and Escherichia have similar but not identical cores.

The biological activity of endotoxin is associated with the lipopolysaccharide (LPS). Toxicity is associated with the lipid component (Lipid A) and immunogenicity is associated with the polysaccharide components. The cell wall antigens (O antigens) of Gram-negative bacteria are components of LPS. LPS elicits a variety of inflammatory responses in an animal. Because it activates complement by the alternative (properdin) pathway, it is often part of the pathology of Gram-negative bacterial infections.

The Limulus assay (LAL) is a well known bioassay in the art to measure LPS concentrations and toxicity. The assay is based on an exquisitely sensitive primitive defense system of the ancient horseshoe crab, Limulus polyphemus. An assay based on this system can be measured by a color change after cleavage of chromogenic or fluorogenic substrates. LAL can used to measure sub-picogram quantities of these microbial products very rapidly with minimal equipment and can detect live, dead and non-cultivable organisms. The blood cells of Limulus, or amebocytes, of the horseshoe crab constitute a primitive "innate" immune defense, binding to the outer cell wall structures of the microbial cell and causing a blood clotting reaction. Soluble LPS, as well as cell wall components of other microbes, such as beta glucans in yeast and fungi, have been shown to cause the horseshoe crab blood to clot. This clotting reaction is now known to be an enzyme cascade whose components are present in granules within the amebocyte. A lysate of the amebocyte is produced by collecting blood cells in a sterile, endotoxin-free method and is available as a commercial product (LAL, Charles River Endosafe, Charleston, S.C.) currently used as an assay for LPS and detoxification of LPS by AP enzymes and compositions comprising sources of AP.

Alkaline Phosphatase (AP):

EC 3.1.3.1 according to IUBMB Enzyme Nomenclature, the common name is alkaline phosphatase (AP), an enzyme that catalyzes the reaction of a phosphate monoester+$H_2O$=an alcohol+phosphate. Other name(s) for AP are alkaline phosphomonoesterase; phosphomonoesterase; glycerophosphatase; alkaline phosphohydrolase; alkaline phenyl phosphatase; orthophosphoric-monoester phosphohydrolase (alkaline optimum). The systematic name of AP is phosphate-monoester phosphohydrolase (alkaline optimum).

AP is a wide specificity enzyme, it also catalyses transphosphorylations. In humans and other mammals, at least four distinct but related alkaline phosphatases are known. They are intestinal, placental, placental-like, and liver/bone/kidney (or tissue non-specific) alkaline phosphatase. The first three are located together on chromosome 2 while the tissue non-specific form is located on chromosome 1. The exact physiological functions of the APs are not known, but AP appears to be involved with a large number of physiological processes, among which the detoxification of LPS through dephosphorylation of the toxicity determining lipid A moiety of LPS. For the current invention, the term alkaline phosphatase may comprise any enzyme exhibiting detoxification of LPS as determined by a Limulus assay or another bioassay. The activity of an AP enzyme or composition or preparation comprising AP can be determined by detoxification of commercially available LPS (for instance Lipopolysaccharide (LPS) from Sigma, Cat. No. L-8274) in vitro, followed by a standard Limulus assay (LAL) before and after AP treatment. Alternatively LPS toxicity reduction through AP activity can be quantitated by means of a bioassay as described by Beumer et al., 2003.

Mucosa is a mucus-secreting membrane lining all body cavities or passages that communicate with the exterior. Mucosa is a moist tissue that lines many organs (such as the intestines) and body cavities (such as nose, mouth, lungs, vagina, bile duct, esophagus) and secretes mucous (a thick fluid). The mucosa, or mucous membrane, is a type of tissue protects body cavities from environmental conditions, pathogens and toxic substances and are usually moist tissues that are bathed by secretions (such as secretions in the bowel, lung, nose, mouth and vagina).

DETAILED DESCRIPTION OF THE INVENTION

The current invention is aimed at providing new methods and compositions for the detoxification of LPS in situ at mucosal tissues in body cavities. A first aim of the in situ detoxification of LPS at mucosal surfaces in the body is to prevent or reduce local inflammatory response at such surfaces. Furthermore, the LPS that is thus detoxified is no longer available for passage through mucosal layers and thus cannot enter the circulation where it will exert its toxic effects and/or cause a further local and/or systemic inflammatory response. Detoxification may also comprise neutralising or complexation of LPS by AP, which by close proximity may form a detoxified composition. The methods comprise the use of sources of alkaline phosphatase, which is known to be a potent means for LPS detoxification. A source of AP can be any AP enzyme, or any composition comprising the AP enzyme and any means which is capable of producing a functional AP enzyme in the context of the current invention, such as DNA or RNA nucleic acids encoding an AP enzyme. The nucleic acid encoding AP may be embedded in suitable vectors such as plasmids, phagemids, phages, (retro)viruses, transposons, gene therapy vectors and other vectors capable of inducing or conferring production of AP. Also native or recombinant micro-organisms, such as bacteria, fungi, protozoa and yeast may be applied as a source of AP in the context of the current invention.

In a first embodiment the invention provides a method for the prevention or reduction of toxicity LPS at a mucosal lining of a mammalian body cavity comprising the step of administering a source of AP at the mucosal layer. For those jurisdictions where methods of treatment are unpatentable by law, the invention likewise pertains to the use of AP as defined above, or the use of a composition containing a source of alkaline phosphatase as defined above. The source of AP is used for the manufacture of a medicament for delivery of AP at a mucosal layer for the prevention or reduction of toxic LPS influx through a mucosal lining of a mammalian body cavity. In an additional embodiment the invention provides a method for the prevention or reduction of toxic LPS influx through a mucosal lining of a mammalian body cavity comprising the step of administering a source of AP at the mucosal layer.

In particular the above mentioned method of administering a source of AP at mucosal layers of body cavities is suited for the treatment or profylaxis of LPS mediated or exacerbated diseases, although the method may also be advantageously used for healthy subjects as a prophylactic treatment aimed at the prevention of LPS induced toxicity and/or LPS induced or exacerbated diseases. The beneficial effects of AP administration to reduce toxic LPS levels in body cavities and at mucosal layers according to the current invention will generate a general health promoting effect regardless of the medical condition of the subject treated. The health promoting effect may be further augmented by the consequent decrease in LPS influx through mucosal layers. An LPS mediated or induced disease may be any disease, symptom or group of symptoms caused by LPS toxicity. An LPS exacerbated disease may be any disease or symptom that is not directly caused by LPS or LPS toxicity but a disease which symptoms and clinical features may be aggravated by LPS and the clinical state of the subject suffering from such a disease is worsened by LPS and LPS toxicity.

Preferably the method is aimed at the treatment of an LPS mediated or exacerbated diseases selected from the group consisting of: inflammatory bowel diseases, sepsis/septic shock, systemic inflammatory response syndrome (SIRS), Meningococcemia, trauma/hemorrhagic shock, burn injuries, cardiovascular surgery/cardiopulmonary bypass, liver surgery/transplant, liver disease, pancreatitis, (necrotising) enterocolitis, periodontal disease, pneumonia, cystic fibrosis, asthma, coronary heart disease, congestive heart failure, renal disease, hemolytic uremic syndrome, kidney dialysis, autoimmune diseases, cancer, Alzheimer, rheumatoid arthritis, lupus, systemic lupus erythematosus.

Circulating endotoxin has been detected in patients with inflammatory bowel diseases, in particular in patients diagnosed with Crohn's disease and ulcerative colitis. Its presence is the consequence of the damaged intestinal mucosa and increased LPS influx or gut translocation and causes or exacerbates the inflammatory response in the intestines. Intestinal bacterial translocation and LPS gut translocation is also observed in acute pancreatitis and liver diseases caused by cirrhosis, alcohol abuse, obstructive jaundice and other hepatic conditions. Endotoxin has also been implicated in the development of periodontal disease, where it penetrates the gingival epithelium/mucosa, ensuing a local inflammatory response. In a preferred embodiment the method comprises oral administration of a source of AP to reduce LPS toxicity at and/or passage of LPS through the mucosa.

The preferred mode of administration comprises the use of pharmaceutical compositions comprising sources of AP, which may be delivered in a daily doses regimen to reduce toxic LPS levels in the lumen of the GI tract for a prolonged period of time. Preferably the pharmaceutical compositions comprise an enteric coating to protect AP from the detrimental effects of gastric juices (pH 1.0 to 2.5) and ensure efficient delivery of AP at the mucosa of the intestinal tract. More preferably, the pharmaceutical composition is a source of AP comprised within an enteric coat.

Enteric coatings arrest the release of the active compound from orally ingestible dosage forms. Depending upon the composition and/or thickness, the enteric coatings are resistant to stomach acid for required periods of time before they begin to disintegrate and permit slow release of AP (drug) in the lower stomach or upper part of the small intestines. Examples of some enteric coatings are disclosed in U.S. Pat. No. 5,225,202 (incorporated by reference). Examples of enteric coatings comprise beeswax and glyceryl monostearate; beeswax, shellac and cellulose, optionally with neutral copolymer of polymethacrylicacid esters; copolymers of methacrylic acid and methacrylic acid methylesters or neutral copolymer of polymethacrylic acid esters containing metallic stearates (for references enteric coatings see: U.S. Pat. Nos. 4,728,512, 4,794,001, 3,835,221, 2,809,918, 5,225,202, 5,026,560, 4,524,060, 5,536,507). Most enteric coating polymers begin to become soluble at pH 5.5 and above, with a maximum solubility rates at pH above 6.5. Enteric coatings may also comprise subcoating and outer coating steps, for instance for pharmaceutical compositions intended for specific delivery in the lower GI tract, i.e. in the colon (pH 6.4 to 7.0, ileum pH 6.6), as opposed to a pH in the upper intestines, in the duodenum of the small intestines the pH ranges 7.7-8 (after pancreatic juices and bile addition). The pH differences in the intestines may be exploited to target the enteric-coated AP composition to a specific area in the gut. It also allows the selection of a specific AP enzyme that is most active at a particular pH in the intestine. For instance CIAP (calf intestinal AP) and human placenta (HPLAP) AP are most active at alkaline pH 8.2 in the small intestinal duodenum, jejunum and ileum, whereas milk derived AP and Bone/Liver Kidney or Tissue non specific AP (TSN AP) are most active at neutral pH and better suited for treatment of the colon (pH 7.4).

The most preferred mucosal tissues to be treated according to the current invention are the mucosal tissues lining the intestinal tract body cavities. Orally administered AP is delivered at the mucosal tissues of the GI tract, which comprises the esophagus, stomach, the small intestines or bowel, (duodenum, jejunum, ileum) and large intestines or colon (caecum, ascending colon, transverse colon, descending colon, sigmoid colon, rectum and anus). Within the scope of the current invention, also mucosal tissues lining the mouth, the ducts of the bile and the pancreas are part of the intestinal tract and may be treated according to method of the current invention.

The compositions comprising a source of AP according to the current invention are particularly suited for oral administration to prevent treat, reduce, treat or alleviate inflammatory diseases of the gastrointestinal tract. Inflammatory diseases of the gastrointestinal tract may be induced and/or exacerbated significantly by the influx of LPS. A reduction in the amount of toxic LPS in the lumen of the intestines by administration of sources of AP will, through detoxification of the lipid A moiety of LPS, result in a corresponding decrease in the systemic influx of toxic LPS in the circulation of a subject. In a most preferred embodiment, the oral administration of sources of AP are particularly preferred for the prophylaxis or treatment of the following inflammatory disease of the gastrointestinal tract: Crohn's disease, colitis, (necrotizing) enterocolitis, colitis ulcerosa, hepatobiliary disease, hepatitis B, hepatitis C, liver cirrhosis, liver fibrosis, bile duct inflammation, biliary obstruction, pancreatitis, acute pancreatitis, peritonitis and periodontal disease.

In another embodiment of the invention, a source of AP is orally administered to subjects who suffer from an increased mucosal permeability of the gastrointestinal tract. Increased mucosal permeability of the GI tract is often the result of a decreased perfusion or ischemia of the intestines. Ischemia, a lack of oxygen supply by the bloodstream, may be caused by heart failure, injuries, trauma or surgery. Ischemia of the intestines results in a malfunctioning of the mucosa and a consequential increase in the influx or translocation of toxic LPS from the gut, resulting in both local and systemic toxicity and inflammation. The toxicity and inflammatory response may even further enhance the mucosal permeability, resulting in a vicious circle. Increased mucosal permeability of the GI tract may be the result of inflammatory bowel diseases or other pathological conditions of the GI tract. Oral administration of sources of AP according to the current invention will significantly reduce or abolish this increased influx of toxic LPS by detoxification of LPS in the lumen of the intestinal cavities. Exogenous administration of AP will break the vicious circle of LPS influx through the mucosa, inflammation and enhanced permeability of the mucosa resulting in an enhanced LPS influx. Decreased perfusion or ischemia of the intestines and a concomitant increased LPS influx is observed by the following group of diseases or conditions: burns, trauma and/or wounds which may result from accidents, gunshot or knife wounds, surgery, and in particular surgery with cardiopulmonary bypass. Also malfunctioning of the heart function, such as congenital heart disease, congestive heart failure, coronary heart disease and ischemic heart disease may result in ischemia of the intestines and an increased influx of LPS. It is a preferred embodiment of the current invention to treat subjects suffering from this group of diseases and conditions with timely and regular oral administration of compositions comprising a source of AP to prevent or reduce LPS influx through the intestinal mucosa with an enhanced permeability for LPS.

In another embodiment the current invention is aimed at providing a source of AP at the mucosal lining the respiratory tract. The respiratory tract is another body cavity with a mucosal lining that is exposed to the toxic effects of LPS. LPS, either free or associated with inhaled bacteria, enters the respiratory tract bronchial and pulmonary mucosa via normal respiration, by inhalation of e.g. dust-particles, or from infections of the respiratory tract and mucosal tissues with gram negative bacteria. In addition, tobacco is known to be a rich source of LPS and smoking, either passive or active, may further contribute significantly to the LPS burden of the bronchial and pulmonary mucosa. Under normal conditions this LPS is detoxified by the local mucosal immune defense system in the respiratory tract. Therefore, in another preferred embodiment the current invention pertains to the administration of a source of AP via inhalation to the bronchial and pulmonary mucosa to prevent or reduce LPS influx through the mucosa of the respiratory tract for those conditions where the normal defense responses to LPS are malfunctioning. The current invention also provides compositions suitable for the delivery of AP at the bronchial and pulmonary mucosa. These compositions are preferably administered to for the prophylaxis or treatment of inflammatory diseases of the respiratory tract. In a most preferred embodiment pulmonary administration of a source of AP according to the current invention is applied to treat or prevent a disease selected from the group consisting of pneumonia, lung infections, asthma, CARA, cystic fibrosis, bronchitis and emphysema. The current invention also provides spraying devices, loaded with a composition comprising a source of AP and optionally various excipients such as propellants, carriers, nebulisers and/or diffusers, suitable for the administration of AP at the pulmonary and bronchial mucosa. Spraying devices, inhalators and nebulisers are known in the art of pharmaceutical formulation and will be obvious to the skilled artisan, reference Remmington's Pharmaceutical Sciences, Mace Publishing Company, Philadelphia Pa., 17th ed. 1985.

In yet another embodiment, the current invention is aimed at the topical administration of a source of AP at a mucosal layer lining a body cavity. In a preferred embodiment the body cavity is the nasal cavity, oral cavity, vagina or rectum. Topical administration of a source of AP at a mucosal tissue lining a body cavity is preferably applied to treat local or systemic inflammatory diseases, and it is particularly preferred for the treatment or prophylaxis of infections of the nasal, vaginal, oral or rectal cavities, sexually transmitted diseases and infections, urinary tract infections, bladder infections and periodontal disease.

The current invention also provides compositions comprising a source of AP, amongst which are pharmaceutical and nutraceutical compositions comprising a source of AP. The compositions may optionally comprise pharmaceutically acceptable excipients, stabilizers, activators, carriers, permeators, propellants, desinfectants, diluents and preservatives. Suitable excipients are commonly known in the art of pharmaceutical formulation and may be readily found and applied by the skilled artisan, references for instance Remmington's Pharmaceutical Sciences, Mace Publishing Company, Philadelphia Pa., 17th ed. 1985. In a preferred embodiment the compositions comprising a source of AP are suitable for oral administration and comprise an enteric coating to protect the AP from the adverse effects of gastric juices and low pH. Enteric coating and controlled release formulations are well known in the art (references as described above). Enteric coating compositions in the art may comprise of a solution of a water-soluble enteric coating polymer mixed with the active ingredient(s) such as AP and other excipients, which are dispersed in an aqueous solution and which may subsequently be dried and/or pelleted. The enteric coating formed offers resistance to attack of AP by atmospheric moisture and oxygen during storage and by gastric fluids and low pH after ingestion, while being readily broken down under the alkaline conditions which exist in the lower intestinal tract.

AP containing compositions for the delivery of AP at mucosal tissues for detoxification of LPS according to the current invention preferably comprise an eukaryotic AP, more preferably a mammalian AP, which may be of the types tissue non-specific AP, such as liver-bone or kidney type, or tissue specific such as placental AP and intestinal AP. Most preferably the mammalian AP is a human or a bovine AP.

In a preferred embodiment of the current invention the source of AP is AP which is preferably produced or isolated from milk, preferably bovine milk. The milk may be obtained from animals that have been bred or genetically modified to produce elevated levels of AP in their milk as compared to wild-type animals. The preparation of AP enriched fractions from milk is known in the art. For instance the milkfat globule membrane enriched or derived fraction is the preferred AP enriched milk fraction and may be routinely obtained by conventional skimming of raw milk. AP isolated from milk may be formulated in pharmaceutical compositions and in food compositions or in nutraceuticals.

In a preferred embodiment the AP containing composition for oral administration of AP to the mucosa of the gastrointestinal tract according to the current invention is a food product or nutraceutical enriched for AP. In one embodiment the food product may be a plant, fruit or vegetable, optionally genetically modified to contain an enhanced level of AP. In another embodiment the AP containing food product or nutraceutical is a dairy product. In particular preparations and compositions containing non-pasteurised milk or fractions thereof, preferably bovine milk, contain high levels of AP and are particularly suited for oral administration as a source of AP according to the current invention.

The current invention also pertains to a method for the preparation of an AP enriched dairy product, preferably milk, a milk fraction or milk product. The method comprises the fractionation of raw milk, preferably bovine milk, pasteurisation of the fractions not containing or not rich in AP and reformulating said fractions with the unpasteurised, AP rich fractions, to obtain a less perishable and AP enriched dairy product. The non pasteurised AP rich fractions may be sterilised by other means, such as, but not limited to, irradiation with UV-, X- or gamma-rays, filtration, pressure, osmotic pressure, chemicals or antibiotics, ensuring that the AP enzyme remains substantially active and that the milkfraction becomes substantially sterile. This dairy product may be used in compositions or administered directly to subjects suffering from or at risk of developing an LPS mediated or exacerbated disease and/or inflammation. However, the AP emiched dairy product may also be offered to healthy subjects as a pharmaceutical or nutraceutical product for the reduction of toxic LPS in the gastrointestinal tract and for the reduction of LPS influx through the gastrointestinal mucosa.

EXAMPLES

Example 1

The current invention, and in particular the effectiveness of AP enzymes, preparations and compositions, and different modes of administration of AP may be tested in various animal models for inflammatory bowel diseases that are known in the art. Animal models mimicking human IBD comprise antigen-induced colitis and colitis induced by microbials; other inducible forms of colitis, chemical (for instance trinitrobenzene sulphonic acid (TNBS) in Montfrans et al., 2002), immunological and physical and genetic colitis models (transgenic and knock-out models, see for instance SCID-mice, Davis et al., 2003, IL-10 KO mice, Rennick et al., 2000, SAMP1/Yit mouse, Kosiewicz, et al., 2001 and Strober et al., 2001); adoptive transfer models and spontaneous colitis models (Kosiewicz, M. M. et al., 2001).

The chemically induced Dextran Sulphate Sodium (DSS) colitis model was originally described by Okayasu et al; Gastroenterology, 1990: 98, 694-702, and is a model for human ulcerative colitis. The model comprises acute and chronic ulcerative colitis in mice caused by administration of 3-10% DSS in their drinking water. The morphological changes and changes in the intestinal microflora are similar to those seen in clinical cases of ulcerative colitis. The colon damage develops due to a toxic effect of DSS on the epithelial cells and to phagocytosis by lamina propria cells, resulting in production of TNF-alpha and IFN-gamma.

Experimental Design for Acute DSS Colitis:

DSS (MW 40.000 obtained from ICN chemicals) is dissolved in acidified drinking water in a concentration of 5% (w/v) and given ad libitum to female balb/c mice (Harlan). The solution is refreshed every day. After 7 days of treatment, treated and control mice may be sacrificed and the intestines analysed. The total colon is dissected (from caecum to rectum) and its length is recorded. About half of the colon is frozen in liquid nitrogen and cryo sections are made for morphology (HE staining). Also small parts of the spleen and the liver are snap-frozen in liquid nitrogen for immunohistochemical purposes. A small part of the colon is used to prepare tissue homogenates for cytokine measurements. Small colon strips are cultured in RPMI/10% FCS for 24 h in absence or presence of LPS. Cytokine secretion (TNF alpha; IL-1 beta; IFN gamma) in the supernatant is measured using specific ELISA assays. Spleen and mesenteric lymph-nodes are dissected and squeezed to prepare single cell suspensions. 4 Peyer's Patches near the colon are dissected and single cell suspensions are made by use of collagenase. Cells are characterized using flow-cytometric techniques. Spleen cells are cultured for 24 h in RPMI/10% FCS in absence or presence of LPS or ConA. Cytokine secretion (TNF alpha; IL1 beta; IFN gamma) in the supernatant is measured using specific ELISA assays. Feaces are collected and cultured on McConkey agar plates for enterobacteriaceae contents. For total aerobic bacteria content, feaces are cultured on blood agar plates.

Results

The assays described above are used to determine the effectiveness of compositions comprising AP in vivo. Reductions in cytokine secretion are observed; decreases in TNF alpha, Il-1 beta and IFN gamma levels are measured in the inflamed intestines upon oral administration of the alkaline phosphatase rich milkfat globule membrane fraction of bovine milk.

Example 2

AP-Treated Mice Develop Less Severe Colitis after TNBS or DSS Treatment

Materials and Methods:

Experimental Design:

Three independent experiments were performed. For the first DSS experiment 42 eight-week old wild type C57BL/6 mice were obtained and for the TNBS experiment 20 eight-week old wild type BALB/c mice were obtained, from Charles River and from Harlan Nederland (Horst, The Netherlands), respectively. For a second DSS experiment, 72 eight week old C57BL/6 mice were obtained from Charles River Nederland. During the experiments, the mice were housed under standard conditions and they were allowed free access to water and food.

In the first experiment with C57BL/6 mice, colitis was induced by administration of 1.5% (n=18) or 2.5% (n=20) dextran sulphate sodium (DSS) in the drinking water of the mice for one week.

In the BALB/c mice, colitis was induced by rectal administration at day zero and seven of 1 mg 2,4,6-trinitrobenzene sulphonic acid (TNBS) (Sigma Chemical Co, St. Louis, Mo., USA) dissolved in 40% ethanol in PBS using a vinyl catheter that was positioned three centimetres from the anus. Preceding to the instillation, the mice were anaesthetised using isoflurane (1-chloro-2,2,2-trifluoroethyl-isofluranedifluoromethylether) (Abbott Laboratories Ltd., Queen-borough, Kent, UK) and after the instillation the mice were kept vertically for 30 seconds. After 48 hours of the second TNBS administration, the mice were sacrificed.

During the induction of colitis, ten BALB/c and twenty C57BL/6 mice received orally 100 Units of alkaline phosphatase solved in 100 µl of 100 mM Tris (pH 7.8) once a day; the other mice received exclusively 100 µl of 100 mM Tris (pH 7.8). Four C57BL/6 mice were used as a reference control: they got no colitis and no treatment.

For a second DSS experiment, colitis was induced in C57BL/6 mice (n=48) by administration of 2% DSS in the drinking water for 5 days. 24 of these mice received 100 Units of alkaline phosphatase in 250 µl of 100 mM Tris (pH 7.8) once a day from day 5 up to day 14, whereas the other 24 mice received vehicle alone. A group of 24 mice that received normal drinking water and vehicle only served as reference control. This setup was used to investigate the use of AP as a rescue drug, once colitis is established.

In all experiments, the weight and temperature of the mice were recorded daily. After sacrificing the mice, caudal lymph node (CLN) and colon were obtained from the mice. Through a midline incision, the colons were removed and opened longitudinally. After removing the faecal material, the weight of the colons was measured and used as an indicator of disease-related intestinal thickening. The colons were divided in two parts, one of which was used for histological analysis and the other for cytokine detection.

Histological Analysis:

The longitudinally divided colons were fixed in 4% formaldehyde embedded in paraffin for routine histology. Three transverse slices (5 µm), taken from each colonic sample, were stained with haematoxylin-eosine and examined by light microscopy. Colonic inflammation was evaluated in a blind manner by estimating the 1) percentage of involved area, 2) the amount of follicles, 3) oedema, 4) fibrosis, 5) erosion/ulceration, 6) crypt loss and 7) infiltration of granulocytes and 8) monocytes with a maximal score of 26.

The percentage of area involved and the crypt loss was scored on a scale ranging from 0 to 4 as follows: 0, normal; 1, less than 10%; 2, 10%; 3, 10 to 50%; 4, more than 50%. Follicle aggregates were counted and scored as follows: 0 point, 0-1 follicles; 1 point, 2-3 follicles; 2 point, 4-5 follicles; 3 point, more than 6 follicles. Erosions were defined as 0 if the epithelium was intact, 1 for ulceration that involved the lamina propria, 2 ulcerations involving the submucosa, and 3 when ulcerations were transmural. The severity of the other parameters was scored on a scale 0 to 3 as follows: 0, absent; 1, weak; 2, moderate; 3, severe.

Cell Culture:

Caudal lymph node cells of TNBS mice were isolated by passing the lymph node through a 40 µm filter cell strainers (Becton/Dickson Labware, N.J., USA). The isolated lymphocytes were suspended in 4 ml RPMI 1640 medium, including L-glutamine, 10% foetal calf's serum (FCS) and antibiotics (Penicillin G sodium 10000 U/ml, Streptomycin sulphate 25 µg/ml. Amphotericin B 25 µg/ml; Gibco/BRL, Paisley, Scotland). The cells were counted and added to flat-bottom 96-well plates at 2×105 cells per well in a total volume of 200 µl of the same medium. The cells were cultured in the presence of immobilised α-CD3 (1:30 concentration; 145.2C11 clone) and soluble α-CD28 (1:1000 concentration; PharMingen) for 48 hours at 37° C. The supernatant was collected and used for a cytokine bead assay (CBA).

Homogenisation and Enzymatic Determination

Swiss roles of colonic samples that were taken 6 cm from the anus were frozen in the nitrogen. Homogenates were made with a tissue homogeniser in 9 volumes Greenberger lysis buffer (300 mmol/L NaCl, 15 mmol/L Tris, 2 mmol/L MgCl2, 2 mmol/L Triton X-100 (Sigma, St. Louis, Mo.), Pepstatin A, Leupeptin, Aprotinine (Roche, Mannheim, Germany), all 20 ng/mL; pH 7.4). The tissue was lysed for one hour on ice and centrifuged for 7 minutes at 3000 rpm and for 10 minutes at 14000 rpm. The supernatant was collected and stored frozen until the day of enzymatic determination and BD cytokine bead array analysis.

The feces of the mice were collected during the period of colitis. The weight of the feces was recorded and suspended in 0.6 ml of 50 mM glycine buffer with 0.5 mM MgCl2 (pH=9.6 at 25° C.). After centrifugation (10', 13000 rpm), the supernatant was stored frozen until the day of determination of alkaline phosphatase activity.

The activity of alkaline phosphatase in the colon and feces was measured spectrophotometrically, using p-nitrophenyl phosphate as a substrate in 50 mM glycine buffer with 0.5 mM MgCl2 (pH=9.6 at 25° C.). Enzymatic activity was expressed in mU/ml for the colon homogenates and in mU/mg for the feces.

Cytokine Bead Assay (CBA)

A cytokine bead assay was performed to determine simultaneously the production of TNF-α, IFN-γ, IL-2, IL-4 and IL-5 in colon homogenates and CLN cell culture supernatant according to the manufacturers recommendations of Becton Dickinson (BD). Briefly, particles (polystyrene beads) were dyed to five fluorescence intensities. The proprietary dye had an emission wavelength of ~650 nm (FL-3). Each particle was coupled via a covalent linkage based on thiol-maleimide chemistry with an antibody against one of the five cytokines and represented a discrete population, unique in their FL-3 intensity. The Ab-particles served as a capture for a given cytokine in the immuno-assay panel and could be detected simultaneously in a mixture. The captured cytokines were detected via direct immunoassay using five different antibodies coupled to phycoerythrin (PE), which emitted at ~585 nm (FL-2). The standards ranging from 0 to 2000 pg/ml were mixtures of all five cytokines, so that five standard curves were obtained. For each sample and cytokine standard mixture, 10 µl of capture Ab-bead reagent, samples or standard and detector Ab-PE reagent were incubated for three hours and were washed to remove unbound detector Ab-PE reagent before data acquisition using flow cytometry. Two-colour flow cytometric analysis was performed using a FACScan® flow cytometre (Becton Dickinson Immunocytometry Systems (BDIS), San Jose, Calif.). Data were acquired and analysed using Becton Dickinson Cytometric Bead Array (CBA) software.

Statistical Analysis

All data were expressed as the means±the standard deviation. Where indicated Student's t test was used to calculate statistical significance for difference in a particular measurement between different groups. Values of $p<0.05$ were considered statistically significant (*$p<0.05$).

Results

To investigate whether oral AP has therapeutic potential in IBD, the TNBS- and DSS-induced colitis in mice were used as models. As predicted, intrarectal instillation of TNBS and oral administration of DSS resulted in diarrhoea and wasting disease. At day two, two of the ten mice in each of the two treatment groups died (see FIGS. 2 and 3) indicating that AP does not prevent mortality due to the early inflammatory response Two or three days after the initial intrarectal administration of TNBS a delayed hypersensitive responsive type 4 reaction is activated and causes most of the inflammation, which leads to additional mortality. Although AP treatment could not prevent the death of the mice during this first reaction, it prevented additional deaths due to the secondary inflammatory response.

In the groups that received 2% DSS in their drinking water for 5 days with subsequent AP gavage for up to 14 days, 33% of the mice died between day 8 and 10 in the AP treated group. Thereafter no mice died in this group. In the placebo treated group, however, in total 60% of the mice died from day 8 onwards until day 14. Similar to the TNBS model, AP is able to reduce mortality in the later stage of DSS-colitis, but not in the induction phase.

Figure 4:
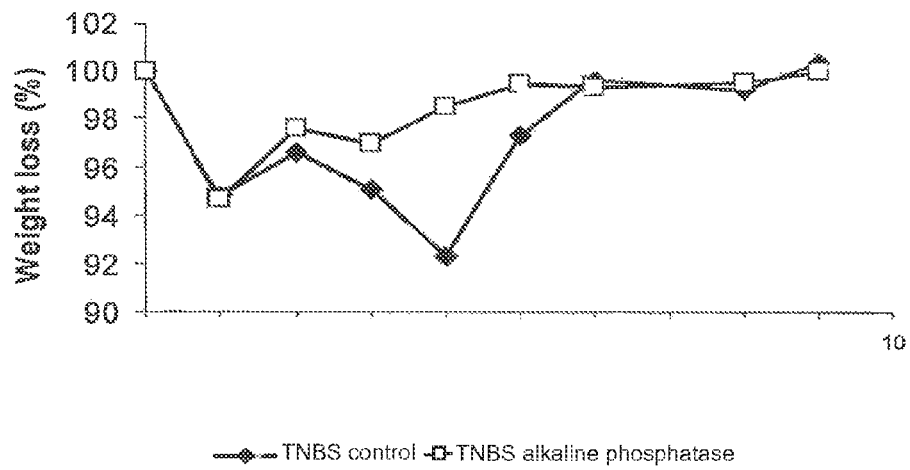

After the first administration of TNBS the weight of the mice has decreased at the first day in both the AP-treated as in the control mice (see FIG. 4). The weight of the control mice, however, was decreased to 92% of their initial weight at day four, whereas the weight of the AP-treated mice was increased to above 98% of their initial weight and was stabilised. At the sixth day, the control mice also reached their initial weight. The effects on weight are thus almost synchronized to the described survival benefits.

Figure 5:
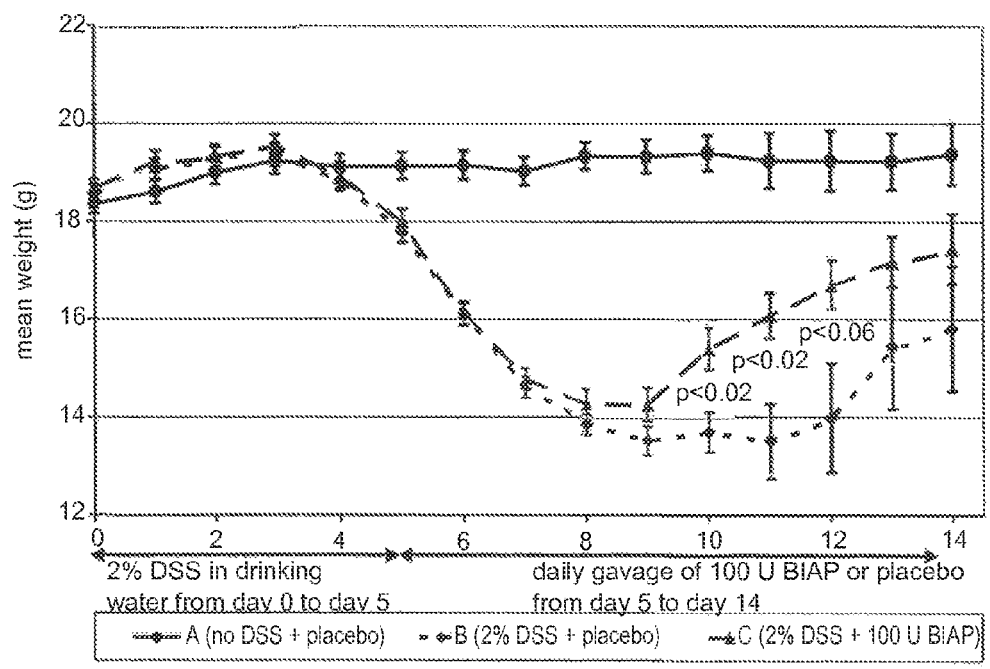

In the DSS studies, only the second group that received 2% DSS and was followed up to 14 days showed statistical significant differences on days 10, 11 and 12 (FIG. 5). The other two groups were followed only up to day 7 and showed, as the former group, no difference between AP treated and untreated groups until that day (data not shown).

Example 3

Cytokine Production and AP Activity were Decreased in Colons of AP-Treated Mice

Colon homogenates of TNBS and DSS mice were analysed for the production of cytokines by a cytokine bead assay to investigate the size of the Th1 response. In contrast to the increased cytokine production in the CLN of AP-treated mice, the production of TNF-α, IFN-γ, IL-2, IL-4 and IL-5 was decreased in the colon homogenates of these mice compared to the control mice, however not significantly (see table 1). The mice with 2.5% DSS-induced colitis confirm similar results, although these results did not reach statistical significance, too. (Data not shown).

TABLE 1

| Cytokine concentrations in colon homogenates measured by CBA | | |
|---|---|---|
| | Control TNBS mice | AP-treated TNBS mice |
| TNF-α | 19.7 ± 12.4 | 10.8 ± 10.8 |
| IFN-γ | 8.2 ± 5.5 | 4.0 ± 4.6 |
| IL-2 | 4.4 ± 2.9 | 2.7 ± 2.6 |
| IL-4 | 15.0 ± 7.0 | 8.9 ± 7.5 |
| IL-5 | 5.9 ± 4.0 | 2.9 ± 3.8 |

TABLE 1-continued

| Cytokine concentrations in colon homogenates measured by CBA | | |
|---|---|---|
| | Control 1.5% DSS mice | AP-treated 1.5% DSS mice |
| TNF-α | 15.6 ± 5.1 | 13.1 ± 5.4 |
| IFN-γ | 100.5 ± 82.3 | 28.4 ± 19.8 |
| | Control 2.5% DSS mice | AP-treated 2.5% DSS mice |
| TNF-α | 89.3 ± 122.3 | 60.7 ± 40.8 |
| IFN-γ | 130.0 ± 85.5 | 83.2 ± 90. |
| IL-2 | 13.2 ± 25.8 | 7.2 ± 6.0 |
| IL-4 | 23.4 ± 42.5 | 24.7 ± 19.2 |
| IL-5 | 19.5 ± 36.8 | 13.9 ± 12.5 |

The production of IL-2, -4 and -5 in the 1.5% DSS mice were almost undetectable (data not shown). The production of TNF-α was decreased in the AP-treated mice compared to the DSS control mice, however not significantly (see FIG. 7). In case of the IFN-γ production, the differences were significant (p<0.05): the IFN-γ production was decreased from 100.5±82.3 pg/ml in DSS control mice to 31.6±21.3 pg/ml in AP-treated mice.

Example 4

Single Oral Dose Pharmacokinetic Assay of BIAP in Mice

Materials and Methods

Subject of investigation was the local and systemic bioavailability after single high dose application of oral BIAP (Bovine intestinal alkaline phosphatase). The test material was delivered as a solution and was stored at 4° C. until use. Dosing dilutions in autoclaved drinking water were prepared freshly on the day of treatment. Autoclaved drinking water was used as control solution.

The black/6 mouse is a suitable rodent species for DSS-induced colitis and is acceptable to regulatory authorities for safety testing. The oral route of administration corresponds to the intended therapeutic use in humans.

The study room and cages were cleaned and disinfected. During the study, the room and cages were cleaned at regular intervals. The room temperature was adjusted to 22±3° C. and the relative humidity was kept between 30% and 70%. These parameters were monitored daily. Artificial light was set to give a cycle of 12 hours light and 12 hours dark with light on at 6:00 a.m. Air was changed about 8 times per hour in the animal room and filtered adequately. The animals were fed ad libitum with SDS D3 pellets, analysed by the supplier for nutrients and contaminants. Drinking water sterilized by autoclaving was continuously available ad libitum via drinking bottles. Consumption is controlled visually on a daily basis.

TABLE 2

| Experimental groups and DSS prerreatment were assigned according to the following table: | | | | | |
|---|---|---|---|---|---|
| Group | Treatment | No. of animals | Card labeling | Conc in drinking water | Volume [ml/kg b.w.] |
| Red | DSS | 29 | A-E (red) | 2% | See Table 3 |
| green | — | 29 | A-E (green) | — | See Table 3 |

TABLE 3

Experimental groups and BIAP treatment were assigned according to the following table:

| Group | From Cage | Treatment | No. of animals | Conc in drinking water | Volume [ml/kg b.w.] | Sacr. Time (min) |
|---|---|---|---|---|---|---|
| Control A | A green | Placebo | 5 | — | 12.5 | 150 |
| Control B | B green | BIAP | 3 | 6000 U/ml | 12.5 | 10 |
| Control C | B green | BIAP | 3 | 6000 U/ml | 12.5 | 30 |
| Control D | C green | BIAP | 3 | 6000 U/ml | 12.5 | 60 |
| Control E | C green | BIAP | 3 | 6000 U/ml | 12.5 | 90 |
| Control F | D green | BIAP | 3 | 6000 U/ml | 12.5 | 120 |
| Control G | D green | BIAP | 3 | 6000 U/ml | 12.5 | 180 |
| Control H | E green | BIAP | 3 | 6000 U/ml | 12.5 | 240 |
| Control I | E green | BIAP | 3 | 6000 U/ml | 12.5 | 360 |
| DSS A | A red | Placebo | 5 | — | 12.5 | 150 |
| DSS B | B red | BIAP | 3 | 6000 U/ml | 12.5 | 10 |
| DSS C | B red | BIAP | 3 | 6000 U/ml | 12.5 | 30 |
| DSS D | C red | BIAP | 3 | 6000 U/ml | 12.5 | 60 |
| DSS E | C red | BIAP | 3 | 6000 U/ml | 12.5 | 90 |
| DSS F | D red | BIAP | 3 | 6000 U/ml | 12.5 | 120 |
| DSS G | D red | BIAP | 3 | 6000 U/ml | 12.5 | 180 |
| DSS H | E red | BIAP | 3 | 6000 U/ml | 12.5 | 240 |
| DSS I | E red | BIAP | 3 | 6000 U/ml | 12.5 | 360 |

According to table 3 all mice except those in the placebo groups in both, control and DSS treated groups received a single oral dose of 75,000 U/kg BIAP per oral gavage (in 250 µl autoclaved drinking water). Placebo groups (n=5) received 250 µl autoclaved drinking water only. All animals were treated once. Before treatment with BIAP, some of the animals were treated with DSS according to table 2.

After blood collection, intestines from the animal were prepared and feces collected from each one third part of the small intestine and from the colon separately. Each sample was dissolved by vigorous vortexing in 1 ml glycine buffer (25 mM; pH=9.6)

These samples were analyzed for alkaline phosphatase content using the an assay for the determination of alkaline phosphatase activity. Paranitrophenyl phosphate, which is colourless, is hydrolysed by alkaline phosphatase at pH 9.6 and 25° C. to form free paranitrophenol, which is coloured yellow. The reaction can be followed spectrophotometrically. The change in optical density at 405 nm per unit time is a measure of the alkaline phosphatase activity. The amount of enzyme causing the hydrolysis of one micromole of paranitrophenyl phosphate per minute at pH 9.6 and 25° C. is defined as one unit. The amount of units present in a sample can be calculated or calibrated against a curve of AP samples with a known AP concentration.

Results

During the pretreatment phase with DSS, mice were weighed daily as an indication for development of colitis. Weight loss of about 10% compared with control mice is used to identify DSS induced colitis. On day 6, mice that were treated for 5 days with DSS had lost around 10% bodyweight (FIG. 8) and were used in the pharmacokinetic experiment to identify local and systemic bioavailability of administered BIAP during colitis. One day later, control mice were used in the same manner.

In order to analyze DSS uptake, drinking bottles were weighed daily before and after refilling of the bottles. The first three days, DSS treated animals consumed approx. the same amount of water as control animals did. Thereafter, DSS mice drank less, probably as a result of decreased well being. However, daily intake of DSS was about 40 mg/mouse, which was shown to be sufficient for induction of colitis in other experiments (see FIG. 9).

The objective of this study was to analyze the local bioavailability in the intestinal tract. For this purpose, on different time points mice were sacrificed and the intestinal tract from duodenum to colon isolated. The small intestine (incl. Duodenum) was divided in two three equal parts. Feces from each part and from the colon was extracted and alkaline phosphatase activity measured. In FIG. 10, the alkaline phosphatase activity in the different parts of the intestine at different time points is shown. No alkaline phosphatase could be measured at any time point in the duodenum and proximal part of the jejunum. This was probably due to the fact that passage through this part takes place within 10 minutes, the first sampling point. At 10 minutes both DSS as well as control animals have peak alkaline phosphatase levels in the distal part of jejunum and proximal part of ileum. Between half an hour and one hour, peak values of AP occur in the distal part of the ileum. In the colon, alkaline phosphatase is increased one and a half hour after gavage and after six hours, most alkaline phosphatase was either excreted or broken down.

Considering that a total of 1350 U was administered per mouse, local bioavailability is estimated in the distal part of the ileum and the colon at 200/1350=15% and 80/1350=6%, respectively. However these values are probably underestimation as they are based on mean peak values of 3 individual mice each (see discussion).

The objective of this study was to estimate the local bioavailability of BIAP after high oral dose administration. The local bioavailability was estimated at 15% in the distal part of the ileum and 6% in the colon. These values are probably grossly underestimated, because values are from individual mice at a given time point and do not represent alkaline phosphatase activity throughout the tract of one mouse followed in time. As a consequence, peak values may be missed in individual mice in a given part of the intestine at a given time point. However, the results as depicted in FIG. 10 clearly demonstrate local bioavailability of AP upon oral administration. These results underscore the feasibility of the method of the current invention to administer to a subject a source of alkaline phosphatase in order to prevent or reduce (toxic) LPS influx through a mucosal lining of a mammalian body cavity.

FIGURES

FIG. 1, explains the model of the current invention in three stages, 1. Mucosa in healthy condition, with normal AP histochemistry and LPS detoxification. 2. Diseased condition, deficient AP staining, insufficient detoxification of LPS by AP, influx/translocation of toxic LPS from the gut into circulation leading to an inflammatory response 3. Restoration of mucosal AP levels and detoxification of LPS by providing an exogenous source of AP.

Figure 2:
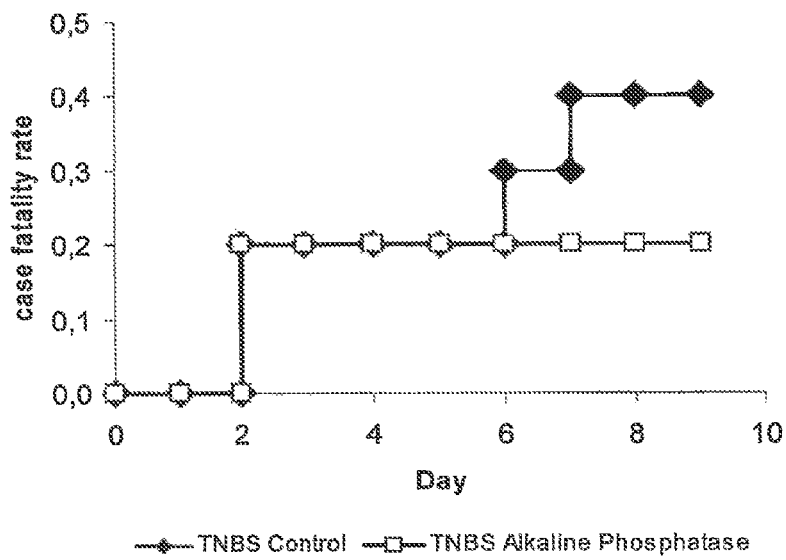

FIG. 2, case fatality rate in mice with TNBS-induced colitis

Figure 3:
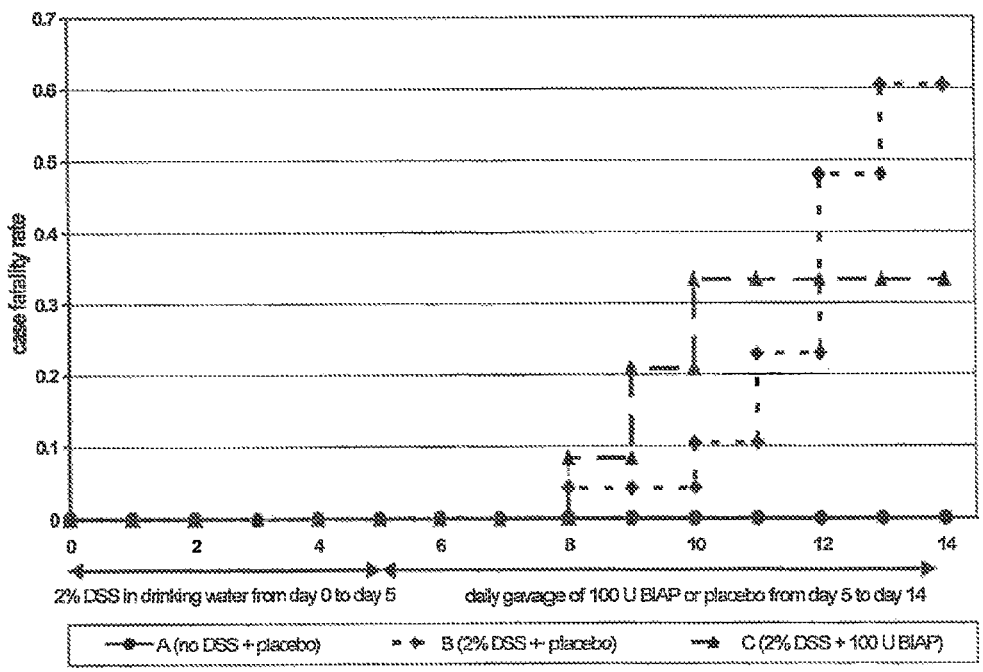

FIG. 3, case fatality rate in mice with DSS-induced colitis

FIG. 4, Weight loss in AP-treated and non-treated mice with TNBS-induced colitis.

Figure 6A:
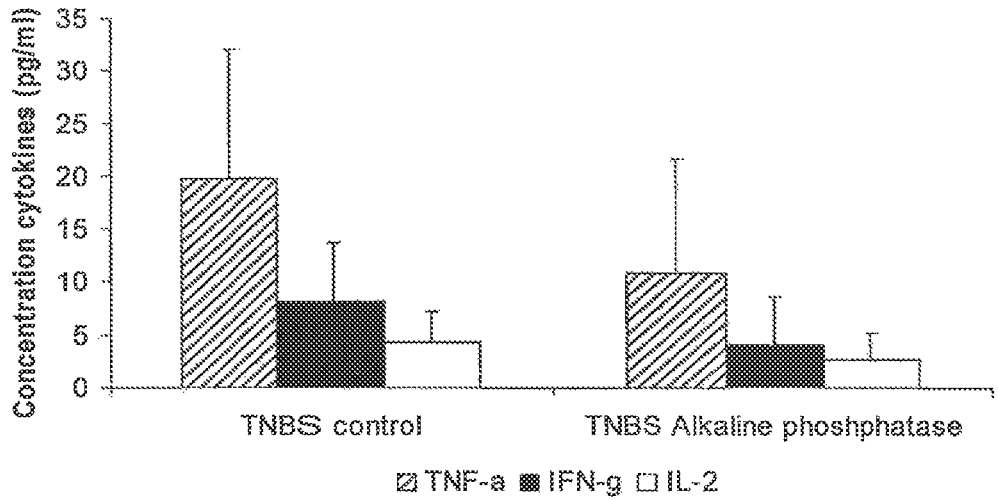

FIG. 5, Weight loss in AP treated and non treated animal with DSS-induced colitis FIG. 6A, Cytokine production in the colon of mice with TNBS-colitis. The TH1 response in the colon.

Figure 6B:
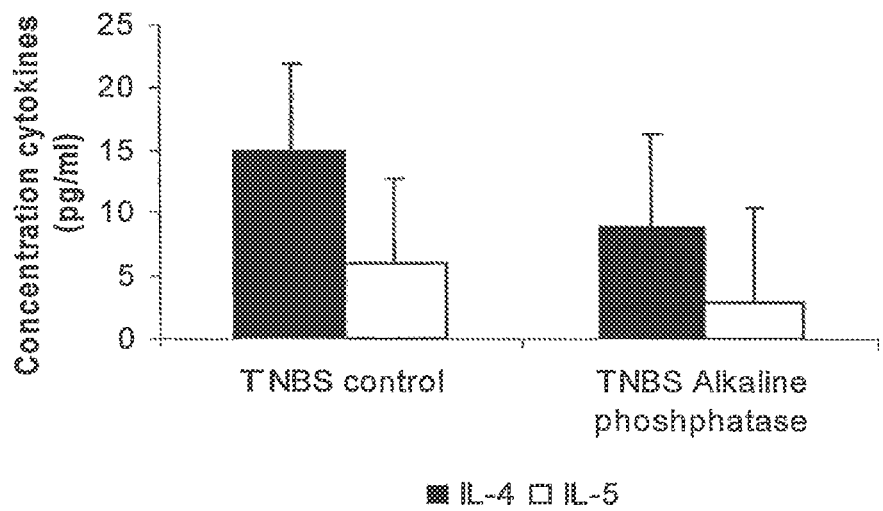

FIG. 6B, Cytokine production in the colon of mice with TNBS-colitis. The TH2 response in the colon.

Figure 7A:
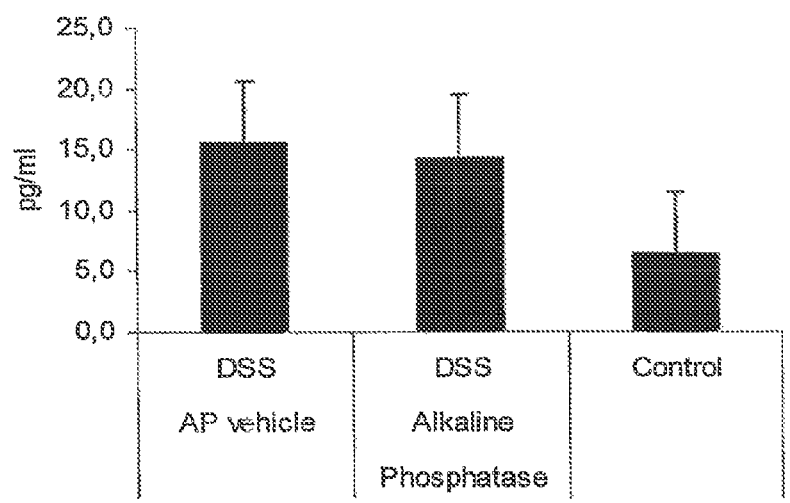

FIG. 7A, The concentration of TNF-α in colon homogenates. The control mice are normal values of non-ill and non-treated mice.

Figure 7B:
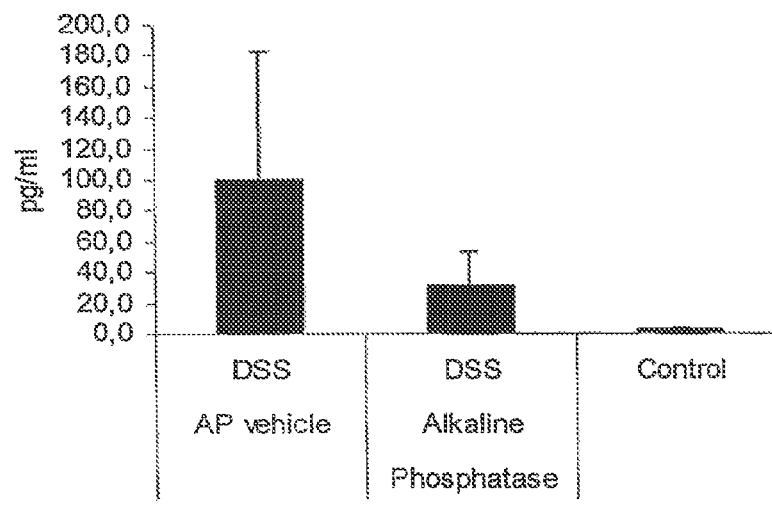
Figure 10A:
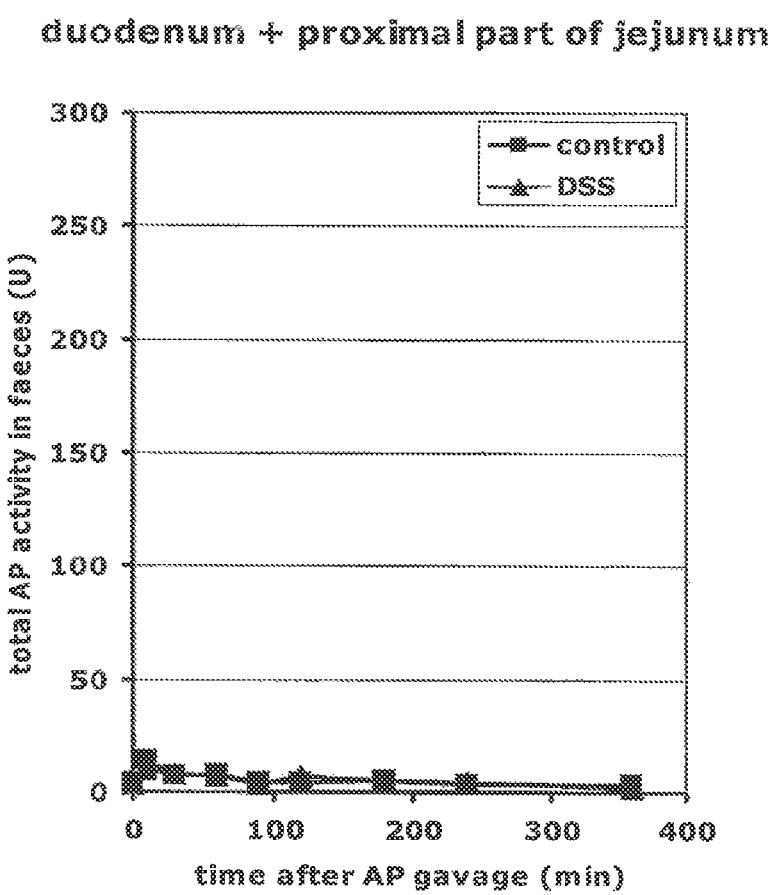
Figure 10B:
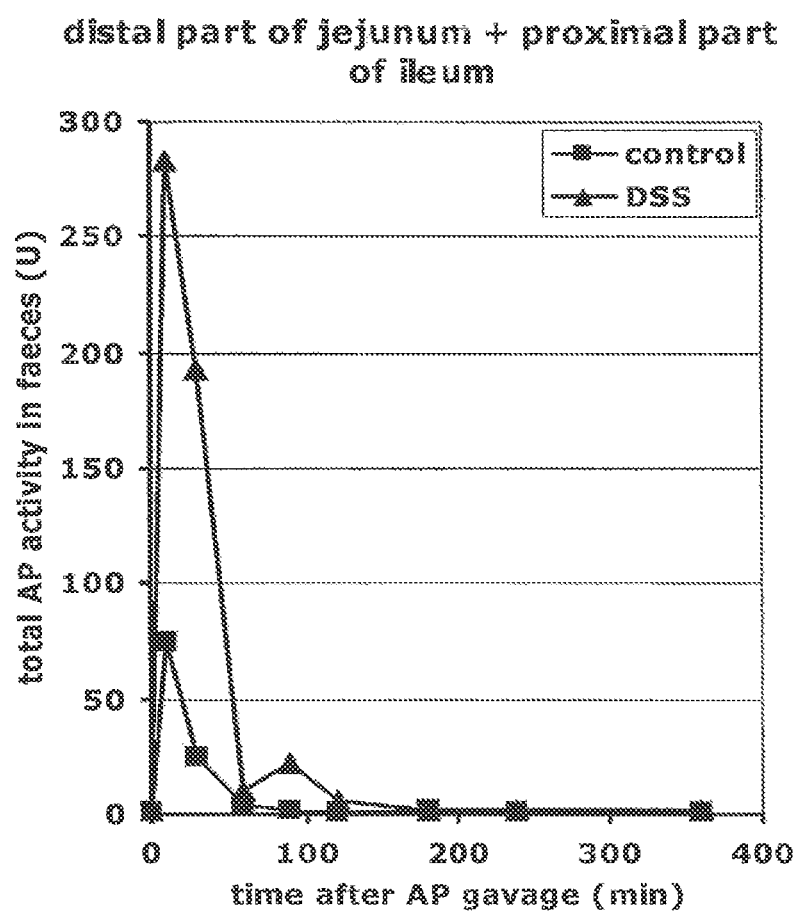
Figure 10C:
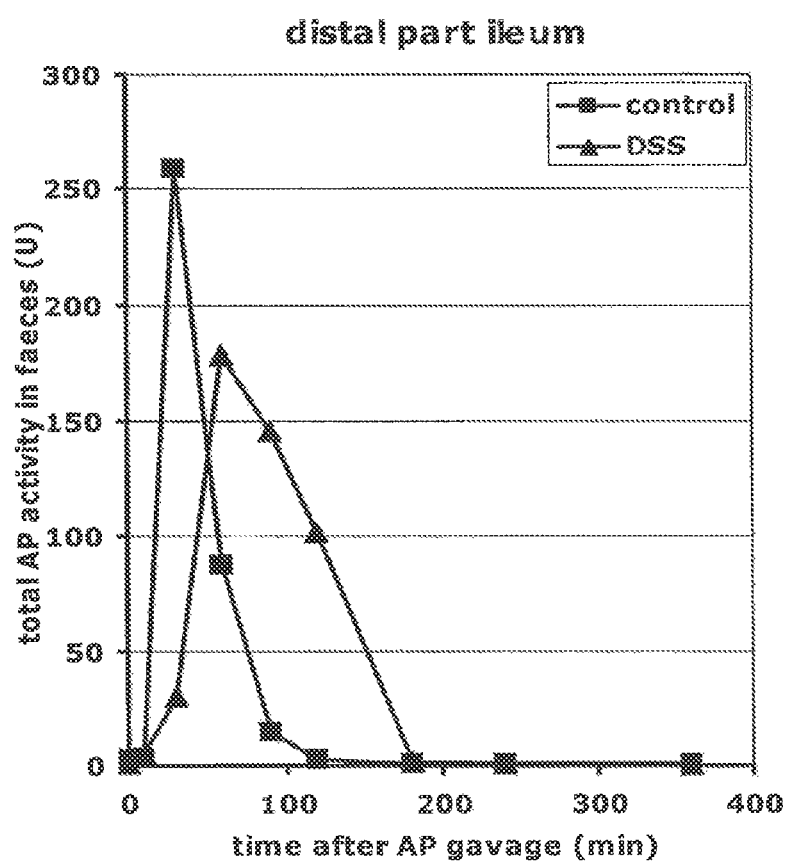
Figure 10D:
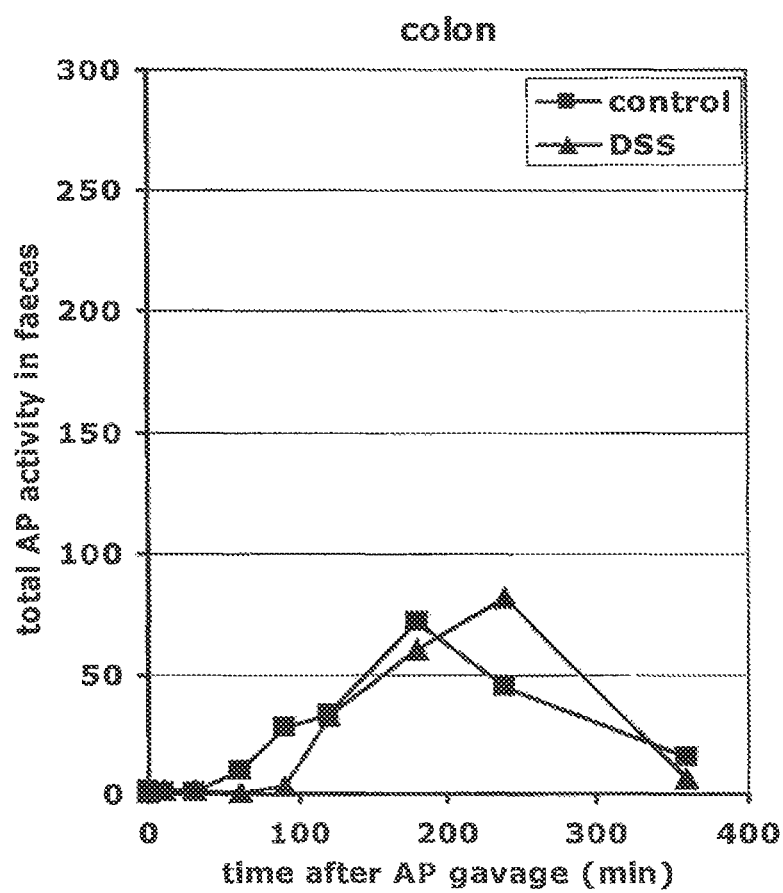

FIG. 7B, The concentration of IFN-γ in colon homogenates. The control mice are normal values of non-ill and non-treated mice.

FIG. 8, DSS treatment decreases bodyweight. Mice were treated either with normal drinking water or with drinking water containing 2% DSS for 5 days. On day six, DSS treated animals had lost around 10% bodyweight compared with control animals and were defined 'colitic'. Shown are mean with standard deviations of 29 animals per group.

FIG. 9, DSS treated mice consume between 40-80 mg DSS per day. Mice were treated either with drinking water or drinking water containing 2% DSS. Drinking bottles were weighed before and after refilling. Values show mean water intake in g/mouse/day.

FIG. 10A-D, Alkaline phosphatase levels in different parts of intestinal tract at different time points after gavage (10A: duodenum+proximal part of jejunum; 10B: distal part of jejunum+proximal part of ileum; 10C: distal part of ileum; and 10D: colon). At different time points after gavage, mice were sacrificed and intestines removed. Feces from different parts of the tract were collected and alkaline phosphatase content measured. Shown are mean values of three mice per time point.

REFERENCES

Alvaro D, Benedetti A, Marucci L, et al. The function of alkaline phosphatase in the liver: regulation of intrahepatic biliary epithelium secretory activities in the rat. Hepatology (United States), August 2000, 32(2) p 174-84

Anh D J, Eden A, Farley J R. Quantitation of soluble and skeletal alkaline phosphatase, and insoluble alkaline phosphatase anchor-hydrolase activities in human serum. Clin Chim Acta. 2001 Sep. 25; 311(2): 137-48.

Bentala H, Verweij W R, Huizinga-Van der Vlag A, van Loenen-Weemaes A M, Meijer D K, Poelstra K. Removal of phosphate from lipid A as a strategy to detoxify lipopolysaccharide. Shock. 2002 December; 18(6): 561-6.

Bentala, H., Verweij, W. R., Brands, R, Huizinga-VanderVlag A, Meijer, D K F, Poelstra, K. Intravenous administration of alkaline Phosphatase to mice challenged with E. coli lipopolysaccharide has prominent protective effects. Submitted for publication Beumer C, Wulferink M, Raaben W, Fiechter D, Brands R, Seinen W. Calf intestinal alkaline phosphatase, a novel therapeutic drug for lipopolysaccharide (LPS)-mediated diseases, attenuates LPS toxicity in mice and piglets. J Pharmacol Exp Ther. 2003 November; 307(2): 737-44.

Paul H. Davis and Samuel L. Stanley, Jr* Cellular Microbiology (2003) 5 (12), 849-860 Breaking the species barrier: use of SCID mouse-human chimeras for the study of human infectious diseases Deng J T, Hoylaerts M F, De Broe M E, van Hoof V O. Hydrolysis of membrane-bound liver alkaline phosphatase by GPI-PLD requires bile salts. Am J Physiol. 1996 October; 271(4 Pt 1): G655-63.

Eichbaum E B, Harris H W, Kane J P, Rapp J H. Chylomicrons can inhibit endotoxin activity in vitro. J Surg Res. 1991 November; 51(5): 413-6.

Ghermay A P, Brady S, Havel R J, Harris H W, Rapp J H. Sepsis increases endocytosis of endotoxin into hepatocytes. Surgery. 1996 August; 120(2): 389-93; discussion 393-4.

Gilman's The Pharmacological Basis of Therapeutics Author: Joel G. Hardman, Joel G. Hardman, Lee E. Limbird, Alfred Goodman Gilman, 13 Aug. 2001 Manufacturer: McGraw-Hill Professional ISBN: 0071354697

Harris H W, Brady S E, Rapp J H. Hepatic endosomal trafficking of lipoprotein-bound endotoxin in rats. J Surg Res. 2002 July; 106(1): 188-95.

Harris H W, Eichbaum E B, Kane J P, Rapp J H. Detection of endotoxin in triglyceride-rich lipoproteins in vitro. J Lab Clin Med. 1991 August; 118(2): 186-93.

Harris H W, Grunfeld C, Feingold K R, Rapp J H. Human very low density lipoproteins and chylomicrons can protect against endotoxin-induced dath in mice. J Clin Invest. 1990 September; 86(3): 696-702.

Harris W S, Hustvedt B E, Hagen E, Green M H, Lu G, Drevon C A. N-3 fatty acids and chylomicron metabolism in the rat. J Lipid Res. 1997 March; 38(3): 503-15.

Harris H W, Rockey D C, Chau P. Chylomicrons alter the hepatic distribution and cellular response to endotoxin in rats. Hepatology. 1998 May; 27(5): 1341-8.

Harris W S. Chylomicron metabolism and omega 3 and omega 6 fatty acids. World Rev Nutr Diet. 1994; 76: 23-5.

Harris W S. omega 3 fatty acids and human chylomicron metabolism. World Rev Nutr Diet. 2001; 88: 163-7.

Harris H W, Kasravi F B. Lipoprotein-bound LPS induces cytokine tolerance in hepatocytes. J Endotoxin Res. 2003; 9(1): 45-50.

Harris W S, Muzio F. Fish oil reduces postprandial triglyceride concentrations without accelerating lipid-emulsion removal rates. Am J Clin Nutr. 1993 July; 58(1): 68-74.

Harris H W, Grunfeld C, Feingold K R, Read T E, Kane J P, Jones A L, Eichbaum E B, Bland G F, Rapp J H. Chylomicrons alter the fate of endotoxin, decreasing tumor necrosis factor release and preventing death. J Clin Invest. 1993 March; 91(3): 1028-34.

Kasravi F B, Brecht W J, Weisgraber K H, Harris H W. Induction of cytokine tolerance requires internalization of Chylomicron-Bound LPS into hepatocytes. J Surg Res. 2003 December; 115(2): 303-9.

Kasravi F B, Welch W J, Peters-Lideu C A, Weisgraber K H, Harris H W. Induction of cytokine tolerance in rodent hepatocytes by chylomicron-bound LPS is low-density lipoprotein receptor dependent. Shock. 2003 February; 19(2): 157-62.

Michele M. Kosiewicz, Cynthia C. Nast, Anasuya Krishnan, Jesus Rivera-Nieves, Christopher A. Moskaluk, Satoshi Matsumoto, Kosuke Kozaiwa, and Fabio Cominelli, Thl-type responses mediate spontaneous ileitis in a novel murine model of Crohn's disease. The Journal of Clinical Investigation, March 2001, Volume 107, Number 6.

Masaya Kobayashi, Mi-Na Kweon, Hirotaka Kuwata, Robert D. Schreiber, Hiroshi Kiyono, Kiyoshi Takeda, and Shizuo Akira Toll-like receptor-dependent production of IL-12p40 causes chronic enterocolitis in myeloid cell-specific Stat3-deficient mice J. Clin. Invest. 111:1297-1308 (2003).

Kumwenda Z L, Wong C B, Johnson J A, Gosnell J E, Welch W J, Harris H W. Chylomicron-bound endotoxin selectively inhibits NF-kappaB activation in rat hepatocytes. Shock. 2002 August; 18(2): 182-8.

Lindsay, C van Montfrans, F Brennanl, S van Deventer, P Drillenburg, H Hodgson4, A to Velde and M Sol Rodriguez Pena, IL-10 gene therapy prevents TNBS-induced colitis Gene Therapy (2002) 9, 1715-1721

Locati M, Riboldi E, Bonecchi R, Transidico P, Bernasconi S, Haribabu B, Morris A J, Mantovani A, Sozzani S. Selective induction of phospholipase D1 in pathogen-activated human monocytes. Biochem J. 2001 Aug. 15; 358(Pt 1): 119-25.

Nauli A M, Zheng S, Yang Q, Li R, Jandacek R, Tso P. Intestinal alkaline phosphatase release is not associated with chylomicron formation. Am J Physiol Gastrointest Liver Physiol. 2003 April; 284(4): G583-7. Epub 2002 Dec. 4.

Okayasu I, Hatakeyama S, Yamada M, Ohkusa T, Inagaki Y, Nakaya R. Related A novel method in the induction of reliable experimental acute and chronic ulcerative colitis in mice. Gastroenterology. 1990 March; 98(3): 694-702

Park Y, Harris W S. Omega-3 fatty acid supplementation accelerates chylomicron triglyceride clearance. J Lipid Res. 2003 March; 44(3): 455-63.

Park Y, Damron B D, Miles J M, Harris W S. Measurement of human chylomicron triglyceride clearance with a labeled commercial lipid emulsion. Lipids. 2001 February; 36(2): 115-20.

Park Y, Grellner W J, Harris W S, Miles J M. A new method for the study of chylomicron kinetics in vivo. Am J Physiol Endocrinol Metab. 2000 December; 279(6): E1258-63.

Poelstra, K., Bakker, W. W., Klok, P. A., Hardonk, M. J., Meijer, D. K. F. (1997) A physiological function for AP: endotoxin detoxification. Laboratory Investigation 76, 319-327.

Poelstra, K., Bakker, W. W., Klok, P. A., Kamps, J. A. A. M., Hardonk, M. J., Meijer, D. K. F. (1997) Dephosphorylation of endotoxin by AP in vivo. American Journal of Pathology 151, 1163-1169

Poelstra, K., W. W. Bakker, M. J. Hardonk and D. K. F. Meijer. (1994) Pharmaceutical composition comprising Phosphatase or a derivative thereof. International patent application PCT/NL94/00189.

Poelstra, K., D. K. F. Meijer, A. Manin't Veld (1998) The LPS-binding moiety of AP as a diagnostic tool in patients with sepsis. International patent application nr PCT/NL98/00722.

Poelstra K, Bakker W W, Klok P A, Hardonk M J, Meijer D K. A physiologic function for alkaline phosphatase: endotoxin detoxification. Lab Invest. 1997 March; 76(3): 319-27.

Read T E, Harris H W, Grunfeld C, Feingold K R, Kane J P, Rapp J H. The protective effect of serum lipoproteins against bacterial lipopolysaccharide. Eur Heart J. 1993 December; 14 Suppl K: 125-9.

Read T E, Harris H W, Grunfeld C, Feingold K R, Calhoun M C, Kane J P, Rapp J H. Chylomicrons enhance endotoxin excretion in bile. Infect Immun. 1993 August; 61(8): 3496-502.

Rennick, D. M. and Fort, M. M., Lessons From Genetically Engineered Animal Models XII. IL-10-deficient (IL-10-/-) mice and intestinal inflammation. Am J Physiol Gastrointest Liver Physiol 278: G829-G833, 2000.

Shao J S, Engle M, Xie Q, et al. Effect of tissue non-specific alkaline phosphatase in maintenance of structure of murine colon and stomach. Microsc Res Tech (United States), Oct. 15, 2000, 51(2) p 121-8

Warren Strober, Kazuhiko Nakamura, and Atsushi Kitani, The SAMPl/Yit mouse: another step closer to modeling human inflammatory bowel disease. The Journal of Clinical Investigation|March 2001|Volume 107|Number 6, 667-69

Xu Q, Lu Z, Zhang X A novel role of alkaline phosphatase in protection from immunological liver injury in mice. Liver (Denmark), February 2002, 22(1) p 8-14

The invention claimed is:

1. A method for preventing or reducing lipopolysaccharide (LPS) toxicity in a subject, comprising administering a composition comprising an alkaline phosphatase (AP) that is suitable for preventing or reducing LPS-induced toxicity in a subject suffering from a liver disease, wherein the AP is delivered to the gastro-intestinal tract of the subject to prevent or reduce said LPS toxicity.

2. The method according to claim 1, wherein the subject suffers from a disease or condition selected from the group consisting of inflammatory diseases of the gastro-intestinal tract, inflammatory bowel disease, sepsis/septic shock, systemic inflammatory response syndrome (SIRS), meningococcemia, trauma/hemorrhagic shock, burn injuries, cardiovascular surgery/cardiopulmonary bypass, liver surgery/transplant, (necrotizing) enterocolitis, periodontal disease, pneumonia, cystic fibrosis, asthma, coronary heart disease, congestive heart failure, renal disease, hemolytic uremic syndrome, kidney dialysis, autoimmune diseases, cancer, Alzheimer, rheumatoid arthritis, lupus, systemic lupus erythematosus, decreased perfusion of the gastro-intestinal tract and ischemia of the gastro-intestinal tract.

3. A method for preventing or reducing lipopolysaccharide (LPS) toxicity in a subject, comprising administering a composition comprising an alkaline phosphatase (AP) that is suitable for preventing or reducing LPS-induced toxicity in a subject suffering from or at risk of suffering from a liver disease, wherein the AP is delivered to the gastro-intestinal tract of the subject to prevent or reduce said LPS toxicity and wherein the liver disease is caused by cirrhosis, alcohol abuse, or obstructive jaundice.

4. A method for preventing or reducing lipopolysaccharide (LPS) toxicity in a subject, comprising administering a composition comprising an alkaline phosphatase (AP) that is suitable for preventing or reducing LPS-induced toxicity in a subject suffering from or at risk of suffering from a liver disease, wherein the AP is delivered to the gastro-intestinal tract of the subject to prevent or reduce said LPS toxicity and wherein the liver disease is selected from the group consisting of hepatobiliary disease, hepatitis B, hepatitis C, liver cirrhosis, liver fibrosis, bile duct inflammation, and biliary obstruction.

5. The method according to claim 1, 3 or 4, wherein the composition is administered orally.

6. The method according to claim 1, 3 or 4, wherein the composition is administered topically to the mucosa of the gastro-intestinal tract.

7. The method according to claim 6, wherein the composition further comprises a pharmaceutically acceptable (i) stabilizer, (ii) activator, (iii) carrier, (iv) permeator, (v) propellant, (vi) disinfectant, (vii) protectant, (viii) diluent, (ix) nutrient or (x) another excipient that promotes AP delivery to said gastro-intestinal tract.

8. The method according to claim 1, 3 or 4, wherein the LPS is detoxified, neutralized, or complexed in situ in the gastro-intestinal tract.

* * * * *